US011339128B2

(12) United States Patent
Petrovic et al.

(10) Patent No.: US 11,339,128 B2
(45) Date of Patent: *May 24, 2022

(54) SUBSTITUTED 4-AMINO-5-(CYCLO-HEXYLOXY)QUINOLINE-3-CARBOXYLIC ACIDS AS SWEET FLAVOR MODIFIERS

(71) Applicant: Firmenich Incorporated, Plainsboro, NJ (US)

(72) Inventors: Goran Petrovic, San Diego, CA (US); Joseph R. Fotsing, San Diego, CA (US); Guy Servant, San Diego, CA (US); Catherine Tachdjian, San Diego, CA (US); Donald Karanewsky, Escondido, CA (US); Binh Vong, San Diego, CA (US); Brant Clayton Boren, San Diego, CA (US); Qing Chen, San Diego, CA (US); Hong Zhang, San Diego, CA (US); Brett Weylan Ching, San Diego, CA (US); Stephanie Lapera, San Diego, CA (US)

(73) Assignee: FIRMENICH INCORPORATED, Plainsboro, NJ (US)

( * ) Notice: Subject to any disclaimer, the term of this patent is extended or adjusted under 35 U.S.C. 154(b) by 104 days.

This patent is subject to a terminal disclaimer.

(21) Appl. No.: 14/925,793

(22) Filed: Oct. 28, 2015

(65) Prior Publication Data

US 2016/0185727 A1 Jun. 30, 2016

Related U.S. Application Data

(60) Provisional application No. 62/076,975, filed on Nov. 7, 2014.

(51) Int. Cl.
| C07D 215/54 | (2006.01) |
| C07D 401/12 | (2006.01) |
| C07D 405/12 | (2006.01) |
| A23L 27/20 | (2016.01) |
| A23L 27/00 | (2016.01) |
| A23L 2/56 | (2006.01) |
| A23L 2/60 | (2006.01) |

(52) U.S. Cl.
CPC .............. *C07D 215/54* (2013.01); *A23L 2/56* (2013.01); *A23L 2/60* (2013.01); *A23L 27/2054* (2016.08); *A23L 27/88* (2016.08); *C07D 401/12* (2013.01); *C07D 405/12* (2013.01); *A23V 2002/00* (2013.01)

(58) Field of Classification Search
CPC .. C07D 215/54; C07D 401/12; C07D 405/12; A23L 27/2054; A23L 27/88; A23L 2/56; A23L 2/60; A23V 2002/00
USPC ................. 426/534, 536, 537, 538
See application file for complete search history.

(56) References Cited

U.S. PATENT DOCUMENTS

| 4,552,883 A | 11/1985 | Bare |
| 4,904,651 A | 2/1990 | Warawa |
| 4,952,584 A | 8/1990 | Thompson et al. |
| 5,006,535 A | 4/1991 | Ife et al. |
| 5,240,934 A | 8/1993 | Hasegawa et al. |
| 5,475,008 A | 12/1995 | Carling et al. |
| 5,593,997 A | 1/1997 | Dow et al. |
| 5,776,942 A | 7/1998 | Furukawa et al. |
| 6,077,851 A | 6/2000 | Bjork et al. |
| 6,194,493 B1 | 2/2001 | Stahrfeldt et al. |
| 6,339,077 B1 | 1/2002 | Hofmeister et al. |
| 6,410,529 B1 | 6/2002 | Chan et al. |
| 7,476,399 B2 | 1/2009 | Tachdjian et al. |
| 7,928,111 B2 | 4/2011 | Tachdjian et al. |
| 8,592,592 B2 | 11/2013 | Tachdjian et al. |
| 9,000,054 B2 | 4/2015 | Tachdjian et al. |
| 9,049,878 B2 | 6/2015 | Tachdjian et al. |
| 9,902,737 B2 | 2/2018 | Tachdjian et al. |
| 2005/0009815 A1 | 1/2005 | Devita et al. |
| 2005/0032158 A1 | 2/2005 | Adler et al. |
| 2005/0084506 A1 | 4/2005 | Tachdjian et al. |
| 2006/0045953 A1 | 3/2006 | Tachdjian et al. |
| 2006/0135552 A1 | 6/2006 | Malherbe et al. |
| 2006/0223843 A1 | 10/2006 | Liu |
| 2007/0104709 A1 | 5/2007 | Li et al. |
| 2008/0026077 A1 | 1/2008 | Hilfinger et al. |
| 2008/0306053 A1 | 12/2008 | Tachjian et al. |
| 2008/0306093 A1 | 12/2008 | Servant et al. |
| 2009/0111834 A1 | 4/2009 | Tachdjian et al. |
| 2009/0292010 A1 | 11/2009 | Shigemura et al. |
| 2010/0273776 A1 | 10/2010 | Lindquist et al. |
| 2012/0252805 A1 | 10/2012 | Chen et al. |
| 2013/0041046 A1 | 2/2013 | Tachdijian et al. |
| 2015/0141527 A1 | 5/2015 | Tachdjian et al. |
| 2015/0265711 A1 | 9/2015 | Tachdjian et al. |

FOREIGN PATENT DOCUMENTS

| EP | 0 096 996 | 12/1983 |
| EP | 0 245 054 | 11/1987 |
| EP | 0 249 301 | 12/1987 |
| GB | 1348259 | 3/1974 |
| GB | 1357449 | 6/1974 |

(Continued)

OTHER PUBLICATIONS

Albrecht, 1972, Antibacterial activity of quinolonecarboxylic acids. II. Synthesis of 1-ethyl-4-quinolone-3-carboxylic acids with fused five-membered heterocyclic rings, Justus Liebigs Annalen der Chemie, 762:55-61.

Anderson, Sep. 2003, The process of structure-based drug design, Chemistry and Biology, 10:787-797.

(Continued)

*Primary Examiner* — Leslie A Wong
(74) *Attorney, Agent, or Firm* — Knobbe, Martens, Olson & Bear, LLP

(57) ABSTRACT

Disclosed herein are 4-amino-5-(cyclohexyloxy)quinoline-3-carboxylic acid compounds having useful as sweet flavor modifiers. Also disclosed herein are ingestible compositions that include one or more of these compounds in combination with a natural or artificial sweetener.

38 Claims, No Drawings

(56) References Cited

FOREIGN PATENT DOCUMENTS

| | | |
|---|---|---|
| JP | 51-48440 | 4/1976 |
| JP | 52-142098 | 11/1977 |
| JP | 57-159784 | 10/1982 |
| JP | 06-199855 | 7/1994 |
| WO | WO 93/10783 | 6/1993 |
| WO | WO 03/037259 | 5/2003 |
| WO | WO 03/045920 | 6/2003 |
| WO | WO 04/004658 | 1/2004 |
| WO | WO 05/015158 | 2/2005 |
| WO | WO 05/077050 | 8/2005 |
| WO | WO 05/086968 | 9/2005 |
| WO | WO 05/123686 | 12/2005 |
| WO | WO 06/002421 | 1/2006 |
| WO | WO 06/007700 | 1/2006 |
| WO | WO 06/053784 | 5/2006 |
| WO | WO 06/097340 | 9/2006 |
| WO | WO 06/124944 | 11/2006 |
| WO | WO 06/125974 | 11/2006 |
| WO | WO 06/138512 | 12/2006 |
| WO | WO 07/126841 | 11/2007 |
| WO | WO 07/147578 | 12/2007 |
| WO | WO 08/154221 | 12/2008 |
| WO | WO 11/106114 | 12/2008 |
| WO | WO 09/063070 | 5/2009 |
| WO | WO 11/075559 | 6/2011 |
| WO | WO 11/123693 | 10/2011 |
| WO | WO 12/021837 | 2/2012 |
| WO | WO 13/158928 | 10/2013 |
| WO | WO 13/158929 | 10/2013 |
| WO | WO 14/0152791 | 9/2014 |
| WO | WO 05/041684 | 5/2015 |

OTHER PUBLICATIONS

Antoine et al.,1972, Antibacterial activity of m-dioxino quinolinecarboxylic acids, I, Chimica Therapeutica, 7(6):434-443.
Atechian et al., New vistas in quinolone synthesis, Tetrahedron, 2007, 63(13):2811-2823.
Baker et al., "Irreversible Enzyme Inhibitors. 192. Hydrophobic Bonding to Some Dehydrogenases with 5-Substituted-4-hydroxyquinoline-3-carboxylic Acids", Journal of Medicinal Chemistry, 1972 15(3), p. 237-241.
Caplus Accession No. 1973:159459 and JP 48-026772 (Yamanouchi Pharmaceutical Co., Ltd) Apr. 9, 1973.
Caplus Accession No. 1975:156277 and JP 49-133399 (Daiichi Seiyaku Co., Ltd.) Dec. 21, 1974.
Caplus Accession No. 1976:421338 and JP 51-008298 (Daiichi Seiyaku Co., Ltd) Jan. 23, 1976.
Caplus Accession No. 1978:170156, 1978.
Caplus Accession No. 2006:125585 and JP 2006036762 (Taisho Pharmaceutical Co Ltd) Feb. 9, 2006.
Caplus Accession No. 2007:1473128, 2007.
CAS Registry No. 933710-66-8, STN Entry date Apr. 30, 2007.
Charvat et al., 1995, Diethyl acetonedicarboxylate—a precursor for the synthesis of new substituted 4-aminoquinolines and fused 4-aminopyridines, Monatshefte fur Chemie, 126:333-340.
Davis "A Search for New Trypanocides. V. Some Derivatives of 10-Phenyl-4:9-diazaphenanthrene.", Journal of the Chemical Society, 1957 p. 828-836.
Doucet-Personeni et al. "A Structure-Based Design Approach to the Development of Novel, Reversible AChE Inhibitors", J. Med. Chem. 2001, 44, pp. 3203-3215.
Fang et al., Hypoglycemic activity and chemical structure of the salicylates, Journal of Pharmaceutical Sciences, 1968, 578(12):2111-2116.
Fujiwara, 2012, Sweeteners interacting with the transmembrane domain of the human sweet-taste receptor induce sweet-taste synergisms in binary mixtures, Food Chemistry, 130:561-568.
Godard et al., "o-Aminoformylquinolines, new heterocyclic synthons", Journal of Heterocyclic Chemistry, 1980 17(3), p. 465-473.

Graves et al., 2002, Discovery of Novel Targets of Quinoline Drugs in the Human Purine Binding Proteome, Mol. Pharmacol. 62(6):1364-1372.
Gressler et al., 2008, Quinolone alkaloids from Waltheria douradinha, Phytochemistry, 69:994-999.
Hayes, Transdisciplinary perspectives on sweetness, Chem. Percept., 1:48-57.
Hirao et al., "Studies on the Synthesis of Quinoline Compounds. IV. Syntheses of 3,3'-Dicarboxy-1,1'-diethyl-4,4'-dioxo-1,1',4,4'-tetrahydropolymethylenedioxydiquinolines", Memoirs of the Kyushu Institute of Technology, Engineering, 1984, No. 14, p. 29-34.
Hoehn et al., Potential antidiabetic agents, Pyrazolo[3,4-b]pyridines, Journal of Medicinal Chemistry, 1973, 16(12):1340-1346.
Iijima et al., "ANDP-2, A Novel Acrinol Degradation Product by Light", Journal of Health Science, 2007 53(6), p. 745-749.
Jensen et al., 1995, Synthesis of 4-Quinolone Derivatives, Acta Chem. Scand. 49:53-56.
Kripalani et al., "Biotransformation in the monkey of cartazolate (SQ 65,396), a substituted pyrazolopyridine having anxiolytic activity", Xenobiotica, 1981 11(7), p. 481-488.
Lalezari, "Synthesis of 4-Aminothieno [2,3-b]pyridine-5-carboxylic Acids (1).", Journal of Heterocyclic Chemistry, 1979 16(3), p. 603-604.
Li et al., Synthesis of new fluroquinolone NM394, Zhongguo Xinyao Zazhi, 2005 14(1):67-69.
Marecki et al., Aug. 1984, Synthesis of 4-substituted aminoquinoline-3-carboxylates as potential antimicrobial agents, Journal of Pharmaceutical Sciences, 73(8):1141-1143.
O'Donnell et al., A study of the analytical behavior of selected synthetic and naturally occurring quinolone using electrospray ionization ion trap mass spectrometry, liquid chromatography and gas chromatography and the construction of an appropriate database for quinolone characterization, Analytica Chimica Acta, 2006, 572(1):63-76.
Pitt, 2009. Heteroaromatic rings of the future, J. Med. Chem. 52:2952-2963.
Pozharskii et al., 1997, Heterocycles in Life and Society, Wiley, pp. 1-6.
Putz et al., Depth-related alkaloid variation in Mediterranean Aplysina sponges, Zeitschrift fuer Natruforschung, C: Journal of Biosciences, 2009, 64(3/4):279-287.
Santilli et al., "2-Oxo-1,8-naphthyridine-3-carboxylic Acid Derivatives with Potent Gastric Antisecretory Properties", Journal of Medicinal Chemistry, 1987 30(12), p. 2270-2277.
Sapelkin et al., 2005, Screening for protein kinase CK2 inhibitors among 3-carboxy-4-aminoquinoline derivatives, Ukrainica Bioorganica Acta 1, 2(1):28-32.
Schaefer et al., "The synthesis of 4-aminoquinolines by intramolecular Friedel-Crafts reaction", Monatshefte fuer Chemie, 1978 109(3), p. 527-635.
Stanczak et al., "Comparison of pharmacophore cinnoline and quinoline systems on the basis of computer calculation and pharmacological screening of their condensed systems", Pharmazie, 2001 56(6), p. 501-505.
Takahashi, Torizo "Syntheses of heterocyclic compounds of nitrogen. LXXV. 3-Quinolinecarboxylic acid derivatives." Yakugaku Zasshi, 1952 72, 1112-1114.
Thiel, May 2004, Structure-aided drug design's next generation, Nature Biotechnology 22(5):513-519.
Titkova et al., "Synthesis of 4-substituted 3-carbethoxy [carboxy]-1,5-naphthyridines, their properties and biological activity, Khimiko-Farmatsevticheskii Zhurnal", 1982 16(6):699-701.
Veronese et al., Nov. 6, 1995, Tin (IV) chloride-promoted synthesis of 4-aminopyrldines and 4-aminoquinolines, Tetrahedron, 51(45):12277-12284.
West, Anthony R., Solid State Chemistry and its Applications, Wiley, New York, 1988, pp. 358 & 365.
Zuleski et al., "Tracazolate metabolites in rat tissue, Drug Metabolism and Disposition", 1985, 13(2), p. 139-147.
International Search Report and Written Opinion dated Apr. 1, 2016 in PCT/US15/057753.

SUBSTITUTED 4-AMINO-5-(CYCLO-HEXYLOXY)QUINOLINE-3-CARBOXYLIC ACIDS AS SWEET FLAVOR MODIFIERS

RELATED APPLICATIONS

Any and all priority claims identified in the Application Data Sheet, or any correction thereto, are hereby incorporated by reference under 37 CFR 1.57. For example, this application claims priority under 35 U.S.C. § 119(e) to U.S. Provisional Application No. 62/076,975, filed on Nov. 7, 2014, the disclosure of which is incorporated herein by reference in its entirety.

BACKGROUND

Field

The present disclosure relates to the fields of chemistry and foods, beverages, and other ingestible compositions. More specifically, the present disclosure relates to compounds useful as flavor enhancers of one or more basic taste modalities.

Background Description

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific.

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness.

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to be modulators of the chemosensory receptors in T1R family and/or their ligands.

There is a need in the art for new compounds suitable for modifying receptor function associated with chemosensory or chemosensory related sensation or reaction.

SUMMARY

Some embodiments provide a compound having the structure of formula (I):

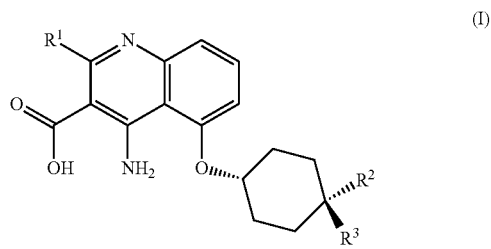

or a salt thereof, wherein:

$R^1$ may be hydrogen or $C_{1-6}$ alkyl optionally substituted with $C_{1-6}$ alkoxy or —OH;

$R^2$ may be selected from the group consisting of hydrogen, —OH, optionally substituted $C_{1-6}$ alkoxy, $C_{1-6}$ alkyl optionally substituted with $C_{1-6}$ alkoxy;

$R^3$ may be selected from the group consisting of hydrogen, —OH, optionally substituted $C_{1-6}$ alkyl, optionally substituted $C_{3-7}$ carbocyclyl, optionally substituted $C_{1-6}$ alkoxy, —(CH$_2$)$_n$NHC(=O)R$^4$, —(CH$_2$)$_n$NR$^5$R$^6$, and —(CH$_2$)$_n$C(=O)NR$^5$R$^6$;

n may be 0, 1, 2 or 3;

$R^4$ may be selected from the group consisting of optionally substituted $C_{3-7}$ carbocyclyl, optionally substituted aryl, optionally substituted 5-10 membered heteroaryl, optionally substituted 3-10 membered heterocyclyl and substituted $C_{1-6}$ alkyl;

$R^5$ may be selected from the group consisting of hydrogen, optionally substituted $C_{1-6}$ alkyl, optionally substituted $C_{3-7}$ carbocyclyl, optionally substituted aryl, and optionally substituted 5-10 membered heteroaryl; and $R^6$ may be selected from the group consisting of hydrogen, substituted $C_{1-6}$ alkyl, optionally substituted $C_{3-7}$ carbocyclyl, optionally substituted aryl and optionally substituted 5-10 membered heteroaryl, with the provisio that when both $R^2$ and $R^3$ are hydrogen then $R^1$ is not methyl or —CH$_2$OH.

Some embodiments provide an ingestible composition, comprising a compound having the structure of formula (I) and a sweetener.

Some embodiments provide method of enhancing sweetness of a sweetener, comprising combining a compound having the structure of formula (I) and a sweetener.

DETAILED DESCRIPTION

In some embodiments, the compounds of formula (I) may have the structure of formula (Ia):

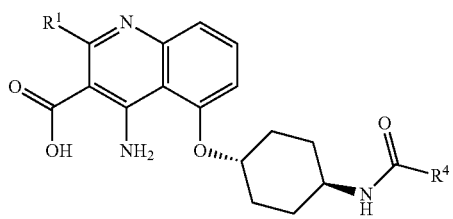

(Ia)

or a salt thereof, wherein $R^1$ may be hydrogen or $C_{1-6}$ alkyl optionally substituted with $C_{1-6}$ alkoxy.

In some embodiments of the compounds of Formula (I) or (Ia), $R^4$ may be selected from the group consisting of optionally substituted $C_{3-7}$ carbocyclyl, optionally substituted aryl, optionally substituted 5-10 membered heteroaryl, optionally substituted 3-10 membered heterocyclyl and $C_{1-6}$ alkyl substituted with one or two $R^{4A}$; each $R^{4A}$ may be independently selected from the group consisting of halo; 5-10 membered heteroaryl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; —$NR^7R^8$; —$SR^9$; and —$OR^9$; $R^7$ may be selected from the group consisting of hydrogen, —C(=O)$OR^{10}$, $C_{1-6}$ alkyl, $C_{3-7}$ carbocyclyl, aryl, 5-10 membered heteroaryl and 3-10 membered heterocyclyl; $R^8$ may be selected from the group consisting of hydrogen, $C_{1-6}$ alkyl, $C_{3-7}$ carbocyclyl, aryl, 5-10 membered heteroaryl and 3-10 membered heterocyclyl; $R^9$ may be selected from the group consisting of hydrogen; $C_{1-6}$ alkyl; $C_{3-7}$ carbocyclyl optionally substituted with one or more substituent selected from the group consisting of halo, $C_1$-$C_6$ alkoxy, $C_1$-$C_6$ haloalkyl, and $C_1$-$C_6$ haloalkoxy; aryl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 5-10 membered heteroaryl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; $C_3$-$C_7$-carbocyclyl-$C_1$-$C_6$-alkyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl-$C_1$-$C_6$-alkyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; aryl($C_1$-$C_6$)alkyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; and 5-10 membered heteroaryl($C_1$-$C_6$)alkyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; and $R^{10}$ may be selected from the group consisting of $C_{1-6}$ alkyl, $C_{3-7}$ carbocyclyl, aryl, 5-10 membered heteroaryl and 3-10 membered heterocyclyl.

In some embodiments of the compounds of Formula (I) or (Ia), $R^4$ may be selected from the group consisting of optionally substituted $C_{3-7}$ carbocyclyl, optionally substituted 3-10 membered heterocyclyl and $C_{1-6}$ alkyl substituted with one or two $R^{4A}$; each $R^{4A}$ may be independently selected from the group consisting of 5-10 membered heteroaryl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; —$NR^7R^8$; —$SR^9$; and —$OR^9$; $R^7$ may be selected from the group consisting of hydrogen, —C(=O)$OR^{10}$ and $C_{1-6}$ alkyl; $R^8$ may be selected from the group consisting of hydrogen and $C_{1-6}$ alkyl; $R^9$ may be selected from the group consisting of hydrogen; $C_{1-6}$ alkyl; $C_{3-7}$ carbocyclyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; and $C_3$-$C_7$-carbocyclyl-$C_1$-$C_6$-alkyl optionally substituted with one or more substituent selected from the group consisting of halo, $C_1$-$C_6$ alkyl, $C_1$-$C_6$ alkoxy, $C_1$-$C_6$ haloalkyl, and $C_1$-$C_6$ haloalkoxy; and $R^{10}$ may be $C_{1-6}$ alkyl.

In some embodiments of the compounds of Formula (I) or (Ia), $R^4$ may be optionally substituted $C_{3-7}$ carbocyclyl or optionally substituted 3-10 membered heterocyclyl.

In some embodiments of the compounds of Formula (I) or (Ia), $R^4$ may be $C_{3-6}$ carbocyclyl or 4-7 membered heterocyclyl.

In some embodiments of the compounds of Formula (I) or (Ia), $R^4$ may be cyclobutyl or pyrrolidin-2-yl.

In some embodiments of the compounds of Formula (I) or (Ia), $R^4$ may be $C_{1-6}$ alkyl substituted with —$NR^7R^8$; $R^7$ may be hydrogen or —C(=O)$OR^{10}$; $R^8$ may be selected from the group consisting of hydrogen and $C_{1-3}$ alkyl; and $R^{10}$ may be selected from the group consisting of $C_{1-6}$ alkyl, $C_{3-7}$ carbocyclyl, aryl, 5-10 membered heteroaryl and 3-10 membered heterocyclyl. In some embodiments, $R^4$ may be $C_{1-3}$ alkyl substituted with —$NR^7R^8$; and $R^7$ may be —C(=O)$OR^{10}$. In some embodiments of the compounds of Formula (I) or (Ia), $R^7$ may be selected from the group consisting of hydrogen, $C_{1-6}$ alkyl, $C_{3-7}$ carbocyclyl, aryl, 5-10 membered heteroaryl and 3-10 membered heterocyclyl.

In some embodiments of the compounds of Formula (I) or (Ia), $R^4$ may be $C_{1-3}$ alkyl substituted with —OH and —$NR^7R^8$; $R^7$ may be hydrogen; and $R^8$ may be selected from the group consisting of hydrogen and $C_{1-3}$ alkyl.

In some embodiments of the compounds of Formula (I) or (Ia), $R^4$ may be $C_{1-3}$ alkyl substituted with —$OR^9$; and $R^9$ may be selected from the group consisting of hydrogen, $C_{1-6}$ alkyl, $C_{3-7}$ carbocyclyl, 3-10 membered heterocyclyl, and $C_3$-$C_6$-carbocyclyl-$C_1$-$C_3$-alkyl.

In some embodiments of the compounds of Formula (I) or (Ia), $R^4$ may be $C_{1-3}$ alkyl substituted with a 5-10 membered heteroaryl optionally substituted with one or more substituents selected from the group consisting of halo, $C_1$-$C_3$ alkyl, $C_1$-$C_3$ alkoxy, $C_1$-$C_3$ haloalkyl, and $C_1$-$C_3$ haloalkoxy.

In some embodiments of the compounds of Formula (I) or (Ia), $R^4$ may be $C_{1-3}$ alkyl substituted with a 3-6 membered heterocyclyl optionally substituted with one or more substituents selected from the group consisting of halo, $C_1$-$C_3$ alkyl, $C_1$-$C_3$ alkoxy, $C_1$-$C_3$ haloalkyl, and $C_1$-$C_3$ haloalkoxy.

In some embodiments, the compounds of formula (Ia) may have the structure of formula (Iaa):

(Iaa)

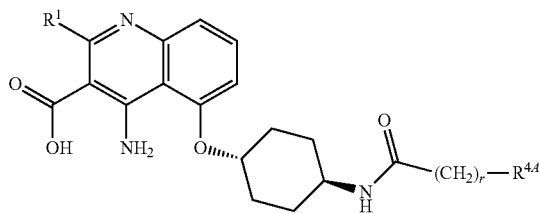

or a salt thereof, wherein: r may be 1, 2, 3 or 4; $R^{4A}$ may be selected from the group consisting of 5-10 membered heteroaryl, 3-10 membered heterocyclyl, —$NR^7R^8$, —$SR^9$, and —$OR^9$; $R^7$ may be selected from the group consisting of hydrogen, —C(=O)$OR^{10}$ and $C_{1-6}$ alkyl; $R^8$ may be selected from the group consisting of hydrogen, $C_{1-6}$ alkyl and $C_{3-7}$ carbocyclyl; $R^9$ may be selected from the group consisting of hydrogen, $C_{1-6}$ alkyl, $C_{3-7}$ carbocyclyl, 3-10 membered heterocyclyl, $C_3$-$C_7$-carbocyclyl-$C_1$-$C_6$-alkyl, 3-10 membered heterocyclyl-$C_1$-$C_6$-alkyl, and 5-10 membered heteroaryl($C_1$-$C_6$)alkyl; and $R^{10}$ may be selected from the group consisting of $C_{1-6}$ alkyl and $C_{3-7}$ carbocyclyl. In some embodiments, $R^{4A}$ may be —$NR^7R^8$; $R^7$ may be —C(=O)$OR^{10}$; $R^8$ may be selected from the group consisting of hydrogen and $C_{1-3}$ alkyl; and $R^{10}$ may be selected from the group consisting of $C_{1-4}$ alkyl, $C_{3-4}$ carbocyclyl, aryl, 5-6 membered heteroaryl and 3-6 membered heterocyclyl.

In some embodiments, $R^{4A}$ may be —$SR^9$ or —$OR^9$; and $R^9$ may be selected from the group consisting of hydrogen, $C_{1-4}$ alkyl, $C_{3-6}$ carbocyclyl, 3-6 membered heterocyclyl, and $C_3$-$C_6$-carbocyclyl-$C_1$-$C_3$-alkyl. In some embodiments, $R^{4A}$ may be —$SR^9$; and $R^9$ is $C_{1-4}$ alkyl. In some embodiments, $R^{4A}$ may be —$OR^9$; and $R^9$ is selected from the group consisting of hydrogen, $C_{1-4}$ alkyl, $C_{3-6}$ carbocyclyl, 4-6 membered heterocyclyl, and $C_3$-$C_5$-carbocyclyl-$C_1$-$C_2$-alkyl.

In some embodiments, the compounds of formula (Ia) may have the structure of formula (Iab):

(Iab)

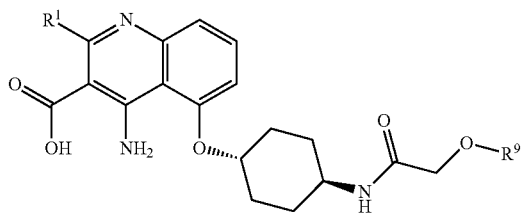

or a salt thereof, wherein: $R^9$ may be selected from the group consisting of hydrogen; $C_{1-6}$ alkyl; $C_{3-7}$ carbocyclyl optionally substituted with one or more substituent selected from the group consisting of halo, $C_1$-$C_4$ alkyl, $C_1$-$C_4$ alkoxy, $C_1$-$C_4$ haloalkyl, and $C_1$-$C_4$ haloalkoxy; 3-10 membered heterocyclyl optionally substituted with one or more substituent selected from the group consisting of halo, $C_1$-$C_4$ alkyl, $C_1$-$C_4$ alkoxy, $C_1$-$C_4$ haloalkyl, and $C_1$-$C_4$ haloalkoxy; $C_3$-$C_7$-carbocyclyl-$C_1$-$C_6$-alkyl optionally substituted with one or more substituent selected from the group consisting of halo, $C_1$-$C_4$ alkyl, $C_1$-$C_4$ alkoxy, $C_1$-$C_4$ haloalkyl, and $C_1$-$C_4$ haloalkoxy. In some embodiments, $R^9$ may be selected from the group consisting of hydrogen, $C_{1-6}$ alkyl, $C_{3-7}$ carbocyclyl, 3-6 membered heterocyclyl and $C_3$-$C_6$-carbocyclyl-$C_1$-$C_3$-alkyl.

In some embodiments, the compounds of formula (I) may have the structure of formula (Ib):

(Ib)

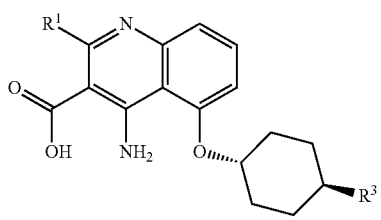

or a salt thereof, wherein $R^1$ may be hydrogen or $C_{1-6}$ alkyl optionally substituted with $C_{1-6}$ alkoxy; $R^3$ may be selected from the group consisting of —OH, $C_{3-7}$ carbocyclyl, $C_{1-3}$ alkoxy, —$CH_2NHC(=O)R^4$, —$CH_2NH_2$, —$NHR^6$, and $C_{1-6}$ alkyl optionally substituted with —OH or $C_{1-3}$ alkoxy; $R^4$ may be $C_{1-3}$ alkyl substituted with $C_{1-3}$ alkoxy; and $R^6$ may be hydrogen or optionally substituted 5-10 membered heteroaryl. In some embodiments, $R^3$ may be selected from the group consisting of —OH, $C_{1-3}$ alkoxy, —$NHR^6$, and $C_{1-6}$ alkyl optionally substituted with —OH or methoxy; and $R^6$ is 5-10 membered heteroaryl. In some embodiments, $R^3$ may be —$NHR^6$; and $R^6$ is pyridin-2-yl or pyrimidin-2-yl. In some embodiments, $R^3$ may be selected from the group consisting of —OH, $C_{1-3}$ alkoxy, and $C_{1-6}$ alkyl.

In some embodiments, the compounds of formula (I) may have the structure of formula (Ic):

(Ic)

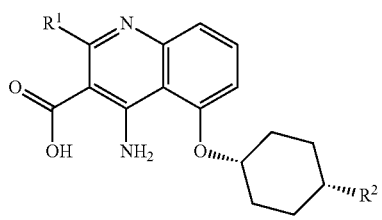

or a salt thereof, wherein $R^1$ may be hydrogen or $C_{1-6}$ alkyl optionally substituted with $C_{1-6}$ alkoxy; and $R^2$ may be selected from the group consisting of —OH, optionally substituted $C_{1-6}$ alkoxy, $C_{1-6}$ alkyl optionally substituted with $C_{1-6}$ alkoxy. In some embodiments, $R^3$ may be selected from the group consisting of —OH, $C_{1-3}$ alkoxy, and $C_{1-6}$ alkyl optionally substituted with methoxy. In some embodiments, $R^3$ may be $R^3$ is —OH or methoxy. In some embodiments, $R^3$ may be $C_{1-4}$ alkyl optionally substituted with methoxy.

In some embodiments of formulas (I), (Ia), (Iaa), (Iab), (Ib), and (Ic), $R^1$ may be hydrogen, methyl, ethyl, or —$CH_2OCH_3$.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Solvate" refers to the compound formed by the interaction of a solvent and a compound described herein or salt thereof. Suitable solvates are physiologically acceptable solvates including hydrates.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "substituted alkyl" refers to an alkyl group substituted with one or more substituents independently selected from $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-

$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methylpropenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—$N(R_A)C(=O)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—$N(R_A)C(=S)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-amido" group refers to a "—$N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, 0-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

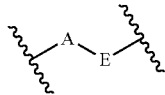

includes the substituent being oriented such that the A is attached at the leftmost attachment point of the molecule as well as the case in which A is attached at the rightmost attachment point of the molecule.

A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

Sweeteners

Sweeteners have a wide range of chemically distinct structures and hence possess varying properties, such as, without limitation, odor, flavor, mouthfeel, and aftertaste.

Natural or artificial sweeteners for use in the formulation comprising a sweetener in combination with a flavor enhancer include but are not limited to natural or synthetic carbohydrates or carbohydrate analogues, including monosaccharides, disaccharides, oligosaccharides, and polysaccharides, and including rare sugars, or sugars in either of the D- or L-conformations, and include, for example, sucrose, fructose, glucose, L-arabinose, L-fucose, L-glucose, L-ribose, D-arabino-hexulose, psicose, altrose, arabinose, turanose, abequose, allose, abrusoside A, aldotriose, threose, xylose, xylulose, xylo-oligosaccharide (such as xylotriose and xylobiose), lyxose, polydextrose, oligofructose, fucose, galacto-oligosaccharide, galactosamine, galactose, gentio-oligosaccharide (such as gentiobiose, gentiotriose, and gentiotetraose), dextrose, cellobiose, D-leucrose, D-psicose, D-ribose, D-tagatose, trehalose (mycose), neotrehalose, isotrehalose, raffinose, idose, tagatose, melibiose, mannan-oligosaccharide, rhamnose, ribose, ribulose, malto-oligosaccharide (such as maltotriose, maltotetraose, maltopentaose, maltohexaose, and maltoheptaose), maltose, sucrose acetate isobutyrate, dextrose, erythrose, erythrulose, deoxyribose, gulose, ketotriose, lactose, lactulose, kestose, nystose, mannose, sucralose, palatinose, polydextrose, sorbose, sugari-dextrose (blended sugar), or talose, or combinations of any two or more of the aforementioned sweeteners.

The sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green *Stevia* powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet *Stevia*-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from sp *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falernum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners.

One of skill in the art will recognize that any one or more of any of the aforementioned sweeteners can be combined in various ratios, amounts, or concentrations to yield a sweetener alone or a combination of two or more sweeteners, which is then combined with one or more flavor modifying compound.

One of skill in the art will recognize that the aforementioned sweeteners for use in a formulation comprising one or more sweetener and one or more flavor modifying compound are provided by way of example and are not intended to be limiting.

Ingestible Compositions

In some embodiments, compounds as disclosed and described herein, individually or in combination, can be used for one or more methods such as modifying receptor function associated with chemosensory or chemosensory related sensation or reaction. Some embodiments provide a method of modulating a chemosensory receptor includes modulating the activity, structure, function, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g.; gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ.

In general, compounds as disclosed and described herein, individually or in combination, can be provided in a composition, such as, e.g., an ingestible composition. In one embodiment, compounds as disclosed and described herein, individually or in combination, can impart a more sugar-like temporal profile and/or flavor profile to a sweetener composition by combining one or more of the compounds as disclosed and described herein with one or more sweeteners in the sweetener composition. In another embodiment, compounds as disclosed and described herein, individually or in combination, can increase or enhance the sweet taste of a composition by contacting the composition thereof with the compounds as disclosed and described herein to form a modified composition. In another embodiment, compounds as disclosed and described herein, individually or in combination, can be in a composition that modulates the sweet receptors and/or their ligands expressed in the body other than in the taste buds.

Some embodiments provide an ingestible composition, comprising the compound of any one of formulas (I), (Ia), (Iaa), (Iab), (Ib), and (Ic), and a sweetener. In some embodiments, the composition further comprises a vehicle. In some embodiments, the vehicle is water. In some embodiments, the compound may be present at a concentration at or below its sweetness recognition threshold. In some embodiments, the sweetener is present in an amount from about 0.1% to about 12% by weight. In some embodiments, the sweetener is present in an amount from about 0.2% to about 10% by weight. In some embodiments, the sweetener is present in an amount from about 0.3% to about 8% by weight. In some embodiments, the sweetener is present in an amount from about 0.4% to about 6% by weight. In some embodiments, the sweetener is present in an amount from about 0.5% to about 5% by weight. In some embodiments, the sweetener is present in an amount from about 1% to about 2% by weight. In some embodiments, the sweetener is present in an amount from about 0.1% to about 5% by weight. In some embodiments, the sweetener is present in an amount from about 0.1% to about 4% by weight. In some embodiments, the sweetener is present in an amount from about 0.1% to about 3% by weight. In some embodiments, the sweetener is present in an amount from about 0.1% to about 2% by weight. In some embodiments, the sweetener is present in an amount from about 0.1% to about 1% by weight. In some embodiments, the sweetener is present in an amount from about 0.1% to about 0.5% by weight. In some embodiments, the sweetener is present in an amount from about 0.5% to about 10% by weight. In some embodiments, the sweetener is present in an amount from about 2% to about 8% by weight. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, an ingestible composition may be a beverage. In some embodiments, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In some embodiments, one or more compounds as described herein and one or more sweetener as described herein may be included in a food or beverage product, wherein the food or beverage product may additionally comprise:

acids, including, for example citric acid, phosphoric acid, ascorbic acid, sodium acid sulfate, lactic acid, or tartaric acid;

bitter ingredients, including, for example caffeine, quinine, green tea, catechins, polyphenols, green *robusta* coffee extract, green coffee extract, whey protein isolate, or potassium chloride;

coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;

preservatives, including, for example sodium benzoate, potassium benzoate, potassium sorbate, sodium metabisulfate, sorbic acid, or benzoic acid;

antioxidants including, for example ascorbic acid, calcium disodium EDTA, alpha tocopherols, mixed tocopherols, rosemary extract, grape seed extract, resveratrol, or sodium hexametaphosphate;

vitamins or functional ingredients including, for example resveratrol, Co-Q10, omega 3 fatty acids, theanine, choline chloride (citocoline), fibersol, inulin (chicory root), taurine, *panax ginseng* extract, guanana extract, ginger extract, L-phenylalanine, L-carnitine, L-tartrate, D-glucoronolactone, inositol, bioflavonoids, *Echinacea*, ginko *biloba*, verba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;

clouding agents, including, for example ester gun, brominated vegetable oil (BVO), or sucrose acetate isobutyrate (SAIB);

buffers, including, for example sodium citrate, potassium citrate, or salt;

flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), or carrageenan.

Some embodiments provide a method of enhancing sweetness of a sweetener, comprising combining a compound of any one of formulas (I), (Ia), (Iaa), (Iab), (Ib), and (Ic) with the sweetener. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In one embodiment, compounds as disclosed and described herein, individually or in combination, can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment, compounds as disclosed and described herein, individually or in combination, can enhance the sweetness of a sweetener under a broad range of pH, e.g., from lower pH to neutral pH. The lower and neutral pH includes, but is not limited to, a pH from about 2.5 to about 8.5; from about 3.0 to about 8.0; from about 3.5 to about 7.5; and from about 4.0 to about 7. In certain embodiments, compounds as disclosed and described herein, individually or in combination, can enhance the perceived sweetness of a fixed concentration of a sweetener in taste tests at a compound concentration of about 50 µM, 40 µM, 30 µM, 20 µM, or 10 µM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener is sucralose.

Some embodiments provide supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products including compounds as disclosed and described herein, individually or in combination.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In some embodiments, compounds as disclosed and described herein, individually or in combination may be included in food or beverage products or formulations. Examples of food and beverage products or formulations include, but are not limited to sweet coatings, frostings, or glazes for ingestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for ingestible compositions, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of sweeteners so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

In some embodiments, compounds as disclosed and described herein, individually or in combination, modulate the sweet taste or other taste properties of other natural or synthetic sweet tastants, and ingestible compositions made therefrom. In one embodiment, the compounds as disclosed and described herein, individually or in combination, may be used or provided in its ligand enhancing concentration(s). For example, the compounds as disclosed and described herein, individually or in combination, may be present in an amount of from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

Some embodiments provide a sweet enhancing composition. The sweet enhancing composition comprises a compound of the present invention in a sweet flavor enhancing amount in combination with a first amount of sweetener, wherein the sweetening is more than the sweetening provided by the first amount of sweetener without the compound. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, provide enhancement of potency of a sweetener at the T1R2/T1R3 taste receptor as measured by an enhancement ratio, defined as the ratio of $EC_{50}$ of the sweetener with and without the compound described herein. In some embodiments, compounds as disclosed and described herein, individually or in combination, provide enhancement ratio of greater than 1 and less than 10. In some embodiments, compounds as disclosed and described herein, individually or in combination, provide an enhancement ratio from 10 to 20. In some embodiments, compounds as disclosed and described herein, individually or in combination, provide an enhancement ratio greater than 20. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Therapeutic Utilities

In some embodiments, compounds as disclosed and described herein, individually or in combination can be used for therapeutic purpose such as modulating a chemosensory receptor and/or its ligand to achieve therapeutic effect. For example, the therapeutic purpose may include modulating a chemosensory receptor and/or its ligand expressed in the body other than in the taste buds.

In some embodiments, a method of modulating a chemosensory receptor and/or its ligand includes modulating the expression, secretion, and/or functional level of T1R expressing cells associated with hormone, peptide, enzyme production by administering compounds as disclosed and described herein, individually or in combination to an individual in need thereof. In one example, the method of the present invention includes modulating the level of glucose, e.g., inhibitors or modulators of a chemosensory receptor such as T1R2/T1R3 can be used to decrease glucose level (e.g., glucose absorption) in a subject by administering compounds as disclosed and described herein, individually or in combination to an individual in need thereof. In some embodiments, the method includes modulating the level of incretins, e.g., agonists or enhancers of a chemosensory receptor such as T1R2/T1R3 can be used to increase glucagon-like peptide 1 (GLP-1) and thus increase the production of insulin by administering compounds as disclosed and described herein, individually or in combination to an individual in need thereof. In some embodiments, the method includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. by administering compounds as disclosed and described herein, individually or in combination to an individual in need thereof. In some embodiments, the method includes modulating the pathways associated with hormones, peptides, and/or enzymes secreted by T1R expressing cells by administering compounds as disclosed and described herein, individually or in combination to an individual in need thereof.

In some embodiments, the method includes modulating the activity of T1R (e.g., T1R1, T1R2, or T1R3) expressing cells, e.g., liver cells (e.g., hepatocytes, endothelial cells, Kupffer cells, Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin), D cells (delta cells, e.g., expressing somatostatin), I cells (e.g., expressing cholescystokinin (CCK), K cells (e.g., expressing gastric inhibitory polypeptide), P/D1 cells (e.g., expressing ghrelin), chief cells (e.g., expressing pepsin), and S cells (e.g., expressing secretin) by administering compounds as disclosed and described herein, individually or in combination to an individual in need thereof. In some embodiments, the method includes increasing the expression level of T1R in T1R expressing cells by administering compounds as disclosed and described herein, individually or in combination to an individual in need thereof. In some embodiments, the method includes increasing the secretion level of T1R expressing cells by administering compounds as disclosed and described herein, individually or in combination to an individual in need thereof.

In some embodiments, the method includes modulation, treatment, and/or prophylactic measure of a condition associated with the gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectial disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc. by administering compounds as disclosed and described herein, individually or in combination to an individual in need thereof.

In some embodiments, the method includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycemia, hyperlipoproteinemias, etc. by administering compounds as disclosed and described herein, individually or in combination to an individual in need thereof.

In some embodiments, the method includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human by administering compounds as disclosed and described herein, individually or in combination to an individual in need thereof.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastrointestinal tract, cold sensation of extremities, difficulty in concentration, impatience, sleep disorder, headache, general malaise, palpitation, night sweat, anxiety, dizziness, vertigo, hot flash, excess sweating, depression, etc.

In some embodiments, the method includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. by administering compounds as disclosed and described herein, individually or in combination to an individual in need thereof. In general, such promotion can be achieved either directly or via increasing the secretion of a regulatory entity, e.g., hormones, etc. by administering compounds as disclosed and described herein, individually or in combination to an individual in need thereof.

In some embodiments, the method includes increasing one or more gastrointestinal functions of a subject, e.g., to improve the quality of life or healthy state of an individual by administering compounds as disclosed and described herein, individually or in combination.

Some embodiments provide a method for treating a respiratory tract infection including administering compounds as disclosed and described herein, individually or in combination to an individual in need thereof. In some embodiments, compounds as disclosed and described herein, individually or in combination can be used for inhibition of respiratory tract infections. Some embodiments provide a method for treating infertility including administering compounds as disclosed and described herein, individually or in combination to an individual in need thereof.

Some embodiments provide a pharmaceutical composition containing a therapeutically effective amount of one or more compounds as disclosed and described herein, or a salt, solvate, and/or prodrug thereof, optionally with a suitable amount of a pharmaceutically acceptable vehicle. In another embodiment, the pharmaceutical composition comprises a therapeutically effective amount of one or more compounds as disclosed and described herein, or a salt, solvate, and/or prodrug thereof and a suitable amount of a pharmaceutically acceptable vehicle so as to provide the form for proper administration to a patient.

In one embodiment, when administered to a patient, the compounds as disclosed and described herein and the optional pharmaceutically acceptable vehicles are sterile. In one embodiment, water is a preferred vehicle when a compound as disclosed and described herein is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound as disclosed and described herein may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

In some embodiments, the pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, 20th Edition, 2000).

For topical administration a compound as disclosed and described herein may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, compounds as disclosed and described herein may be formulated in accordance with routine procedures as a pharmaceutical composition adapted for intravenous administration to human beings. Typically, compounds for intravenous administration are solutions in sterile isotonic aqueous buffer. For injection, a compound may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When a compound is administered by infusion, it can be dispensed, for example, with an infusion bottle containing sterile pharmaceutical grade water or saline. In some embodiments, an ampoule of sterile water for injection or saline can be provided so that the ingredients may be mixed prior to administration when a compound is administered by injection.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

In some embodiments, a compound as disclosed and described herein may also be formulated in rectal or vaginal pharmaceutical compositions such as suppositories or retention enemas, e.g., containing conventional suppository bases such as cocoa butter or other glycerides.

In addition to the formulations described previously, a compound as disclosed and described herein may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

A compound as disclosed and described herein, and/or pharmaceutical composition thereof, will generally be used in an amount effective to achieve the intended purpose. For use to treat or prevent diseases or disorders the compounds as disclosed and described herein and/or pharmaceutical compositions thereof, are administered or applied in a therapeutically effective amount.

In some embodiments, the dosage may be delivered in a pharmaceutical composition by a single administration, by multiple applications or controlled release. In some embodiments, the compounds as disclosed and described herein may be delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound as disclosed and described herein per kilogram body weight.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems.

In some embodiments, the dosage of a compound described herein will preferably be within a range of circulating concentrations that include an effective dose with little or no toxicity.

In certain embodiments, the compounds as disclosed and described herein and/or pharmaceutical compositions thereof can be used in combination therapy with at least one other agent. In some embodiments, a compound as disclosed and described herein and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Some exemplary synthetic methods for preparing the present compounds are illustrated in the Schemes 1 and 2 below.

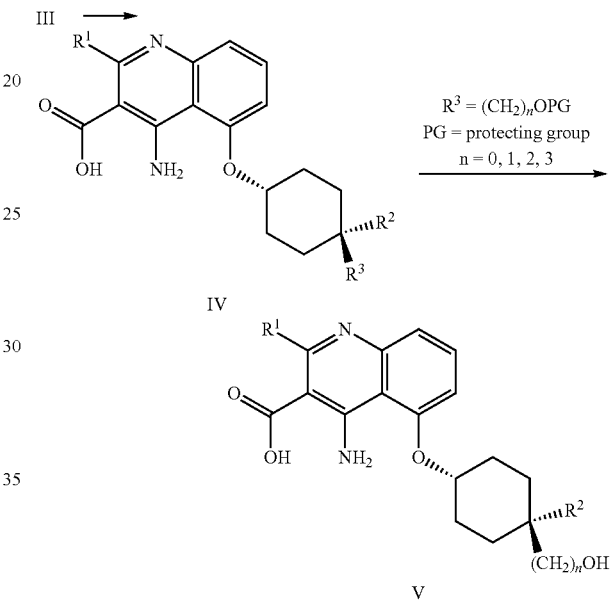

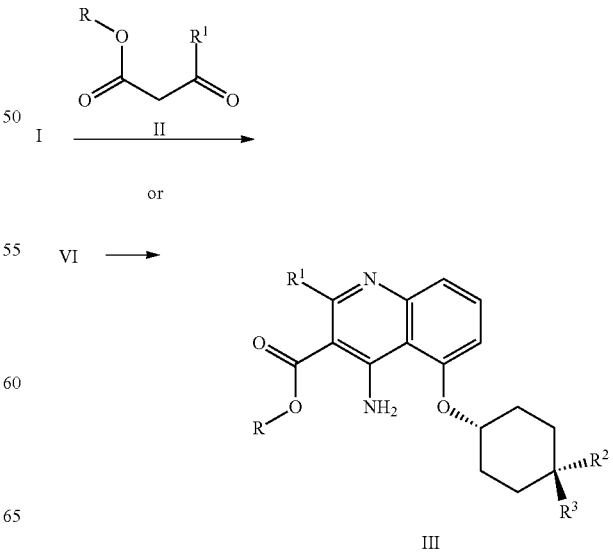

Scheme 1B: Preparation of amine derivatives (VII)

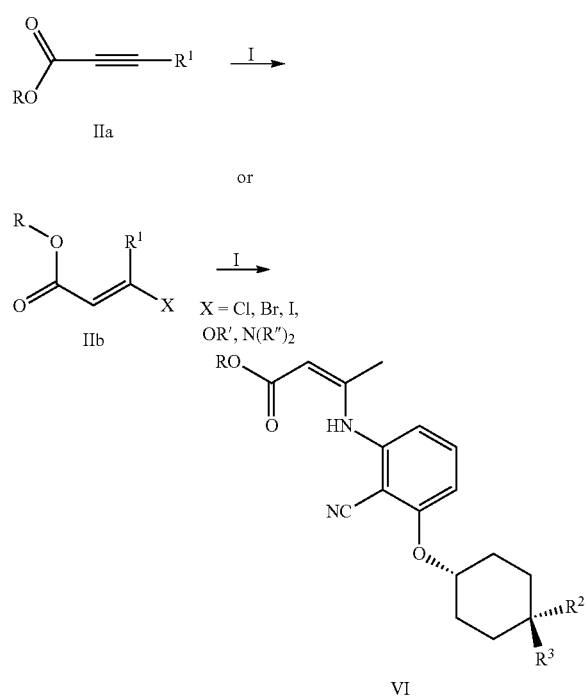

Scheme 1C: Preparation of 2-Aminobenzonitrile Derivatives (I)

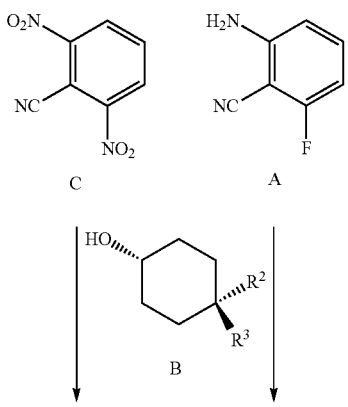

As shown in Scheme 1C, aminobenzonitriles (I), which are key building blocks in the synthesis of 4-aminoquinoline-3-carboxylate derivatives (III) can be synthesized directly from 2-amino-6-fluorobenzonitrile (A) and cyclohexanols (B) in the presence of a base such as NaH and tert-BuOK. Alternatively, the based induced reaction of 2,6-dinitrobenzonitrile (C) and various cyclohexanols (B) followed by a simple nitro reduction of the intermediates 6-nitrobenzonitriles (D) can also yield aminobenzonitriles (I). As shown in Scheme 1A, reacting aminobenzonitriles (I) with acetoacetates (II) in the presence of appropriate Lewis acids such as $SnCl_4$ and $FeCl_3$ can lead to substituted 4-aminoquinoline-3-carboxylate derivatives (III) (Sestili, I. et al. *Eur. J. Med. Chem.* 2004, 39, 1047-1057. Doucet-Personeni, C. et al. *J. Med. Chem.* 2001, 44, 3203-3215. Veronese, A. C. et al. *Tetrahedron* 1995, 51, 12277-12284, and the references cited therein.). As shown in Scheme 1A, aminoquinolines (III) can also be prepared by cyclization of enamine derivatives (VI) (Han, G. F. et al. *Synth. Commun.* 2009, 39, 2492-2505. Tabarrini, O. et al. *Bioorg. Med. Chem.* 2001, 9, 2921-2928. Shutske, G. M. et al. *J. Med. Chem.* 1989, 32, 1805-1813, and references cited therein.). As shown in Scheme 1B, the latter enamine derivatives (VI) can be synthesized via Michael addition of 2-aminobenzonitriles (I) to various α,β-unsaturated carboxylate derivatives (IIa) or (IIb) (MacNab, H. et al. *Synthesis* 2009, 2171-2174. Vicario, J. L. *Synthesis* 2007, 2065-2092, and references cited therein.). As shown in Scheme 1, treatment of various 4-aminoquinoline-3-carboxylates (III) under common saponification methods can lead to the corresponding substituted 4-aminoquinoline-3-carboxylic acid derivatives (IV). When $R^3=(CH_2)_nOPG$ (PG=Protecting Group such as benzyl, Boc, and appropriate carboxamides), the protecting group can be removed under traditional literature procedures to give the corresponding alcohol derivatives (V).

Scheme 2: Preparation of substituted 4-aminoquinoline-3-carboxylic acid derivatives (VII) from Adducts (IV) and Subsequent Conversion into Derivatives (VIII) and (IX)

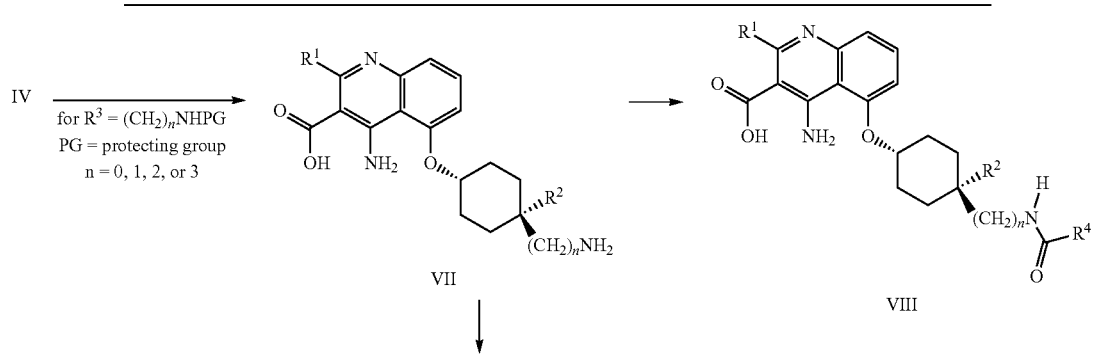

-continued

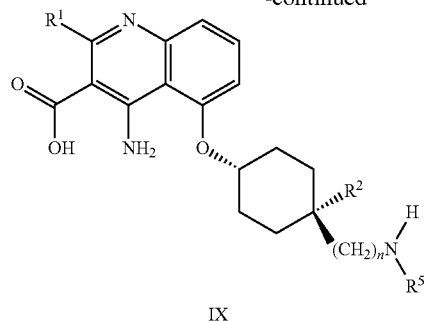

IX

For substituted 4-aminoquinoline-3-carboxylic acid derivatives (IV) with $R^3$=$(CH_2)_n$NHPG (Scheme 2, PG=Protecting Group such as benzyl, Boc, Cbz, . . . ), the protecting groups can be removed using traditional literature procedures to give the corresponding amine derivatives (VII). Adducts (VII) can be further transformed to yield the corresponding carboxamides (VIII) by commonly used amide coupling procedures. Substituted amine derivatives (IX) can also be prepared from (VII) using well documented nucleophilic aromatic substitution protocols (M. Bella et al., J. Am. Chem. Soc. 2005, 127, 3670-3671; F. Tjosaas and A. Fiksdahl, Molecules 2006, 130-133, and the references cited therein.). Alternatively, the conversion of (VII) to (IX) can be performed by widely reported Buckwald-Hartwig or Ullmann-Goldberg C—N coupling methods (J. F. Hartwig, Pure Appl. Chem 1999, 71, 1416-1423; A. R. Muci and S. L. Buchwald, Curr. Chem. 2002, 219, 131-209; A. Klapars et al., J. Am. Chem. Soc. 2002, 124, 7421-7428; E. R. Strieter, J. Am. Chem. Soc. 2005, 127, 4120-4121; C. P. Jones, J. Org. Chem. 2007, 72, 7968-7973 and the references cited therein.).

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1

4-Amino-2-methyl-5-((trans-4-methylcyclohexyl)oxy)quinoline-3-carboxylic acid

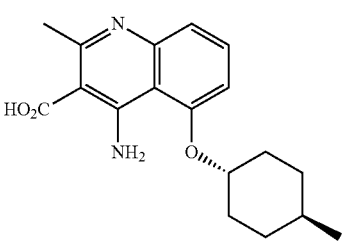

100

To a solution of ethyl 4-amino-2-methyl-5-((trans-4-methylcyclohexyl)oxy)quinoline-3-carboxylate (Example 1a) (1.50 g, 4.3 mmol) in EtOH (20 mL) was added an aqueous 2 M NaOH solution (8.6 mL, 4 equiv.) at room temperature, and the reaction mixture was refluxed for 12 h. After cooling down to room temperature, the solution was neutralized with an aqueous 4M HCl solution (4.3 mL, 17.2 mmol, 4 equiv.). The product was isolated via HPLC (RPC-18, water/acetonitrile gradient), and further purified by re-crystallization from hot EtOH to give 726 mg (54%) of the title compound as a white solid. mp=225-228° C. $^1$H NMR (400 MHz, CD$_3$OD) δ 7.71 (t, J=8.3 Hz, 1H), 7.20 (dd, J=8.4, 0.9 Hz, 1H), 7.13 (dt, J=8.2, 0.8 Hz, 1H), 4.62 (tt, J=10.8, 4.2 Hz, 1H), 2.77 (s, 3H), 2.33-2.20 (m, 2H), 1.93-1.75 (m, 2H), 1.72-1.57 (m, 2H), 1.51 (tdq, J=13.1, 6.5, 3.3 Hz, 1H), 1.27-1.11 (m, 2H), 0.96 (d, J=6.5 Hz, 3H). MS 315 (MH$^+$).

Example 1a

Ethyl 4-amino-2-methyl-5-((trans-4-methylcyclohexyl)oxy)quinoline-3-carboxylate

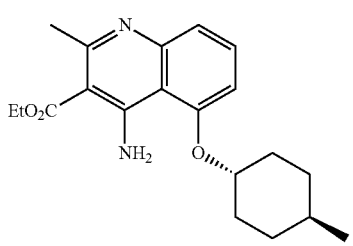

1a

To a solution of 2-amino-6-((trans-4-methylcyclohexyl)oxy)benzonitrile (Example 1b) (1.7 g, 7.4 mmol) and ethyl acetoacetate (1.25 g, 9.62 mmol, 1.3 equiv.) in dry toluene (300 mL) was added tin(IV) chloride (1.7 mL, 14.8 mmol, 2 equiv.) drop-wise at room temperature under nitrogen. After stirring at room temperature for 1 h, the reaction mixture was refluxed for 12 h. Excess toluene was removed under reduced pressure; the residue was then diluted with EtOAc and carefully neutralized with an aqueous 4M NaOH solution to pH 8-10. The heterogeneous solution was stirred for 1 h until all the solids were dissolved. The resulting mixture was filtered through a pad of celite and washed with EtOAc. The organic layer was separated and the aqueous layer was extracted with EtOAc (3×200 mL). The combined organic extract was successively washed with brine, dried over MgSO$_4$, filtered and evaporated under reduced pressure. The residue was purified by silica gel column chromatography (10% MeOH in dichloromethane), to give 1.34 g (52%) of the title compound as yellow oil. $^1$H NMR (400 MHz, DMSO-d$_6$) δ 8.18 (s, 2H), 7.50 (t, J=8.2 Hz, 1H), 7.21 (dd, J=8.3, 1.0 Hz, 1H), 7.02-6.90 (m, 1H), 4.52 (tt, J=10.7, 4.1 Hz, 1H), 4.30 (q, J=7.1 Hz, 2H), 2.54 (s, 3H), 2.19-2.09 (m, 2H), 1.77-1.66 (m, 2H), 1.55-1.35 (m, 3H), 1.31 (t, J=7.1 Hz, 3H), 1.17-1.03 (m, 2H), 0.88 (d, J=6.5 Hz, 3H).

Example 1b

2-Amino-6-((trans-4-methylcyclohexyl)oxy)benzonitrile

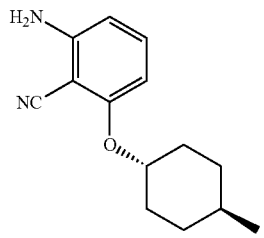

To a suspension of sodium hydride (0.72 g, 18 mmol, 1.2 equiv., 60% in mineral oil) in dry THF (15 mL) was added drop-wise a solution of trans-4-methylcyclohexanol (2.0 g, 18 mmol, 1.2 equiv.) in dry THF (15 mL) at 0° C. under nitrogen. The mixture was stirred at 0° C. for 15 min before warming to room temperature over a 15 min period. The solution was cooled to 0° C. and a solution of 2-amino-6-fluorobenzonitrile (2.0 g, 15 mmol, 1.0 equiv.) in dry THF (15 mL) was added drop-wise. The mixture was stirred for 30 min at room temperature, then refluxed (~90° C.) over 12 h and cooled to room temperature. A saturated aqueous solution of NH$_4$Cl (100 mL) was added and the mixture was extracted with EtOAc (3×100 mL). The combined extract was washed with brine, dried over MgSO$_4$, filtered and concentrated under reduced pressure. The residue was purified by silica gel column chromatography (50% EtOAc in hexane), to give 1.7 g (49%) of the title compound as an oil. $^1$H NMR (400 MHz, DMSO-d$_6$) δ 7.13 (t, J=8.3 Hz, 1H), 6.26 (ddd, J=17.5, 8.5, 0.8 Hz, 2H), 5.91 (s, 2H), 4.25 (tt, J=10.7, 4.2 Hz, 1H), 2.07-1.93 (m, 2H), 1.77-1.58 (m, 2H), 1.45-1.27 (m, 3H), 1.13-0.95 (m, 2H), 0.86 (d, J=6.6 Hz, 3H).

Example 2

4-Amino-5-((trans-4-(methoxymethyl)cyclohexyl)oxy)-2-methylquinoline-3-carboxylic acid

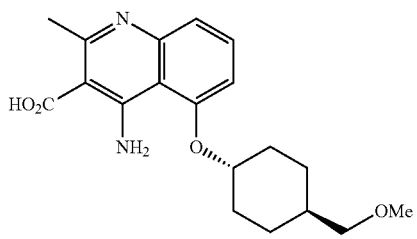

Prepared as in Example 1 from ethyl 4-amino-5-((trans-4-(methoxymethyl)cyclohexyl)oxy)-2-methylquinoline-3-carboxylate (Example 2a). $^1$H NMR (400 MHz, DMSO-d$_6$) δ 8.73 (s, 2H), 7.62 (t, J=8.3 Hz, 1H), 7.22 (d, J=8.3 Hz, 1H), 7.09 (d, J=8.2 Hz, 1H), 4.70-4.50 (m, 1H), 4.21-3.97 (m, 1H), 3.23 (s, 3H), 3.16 (d, J=7.4 Hz, 2H), 2.72 (s, 3H), 2.26-2.08 (m, 2H), 1.88-1.70 (m, 2H), 1.68-1.48 (m, 3H), 1.26-1.02 (m, 2H). MS 345 (MH$^+$).

Example 2a

Ethyl 4-amino-5-((trans-4-(methoxymethyl)cyclohexyl)oxy)-2-methyl quinoline-3-carboxylate

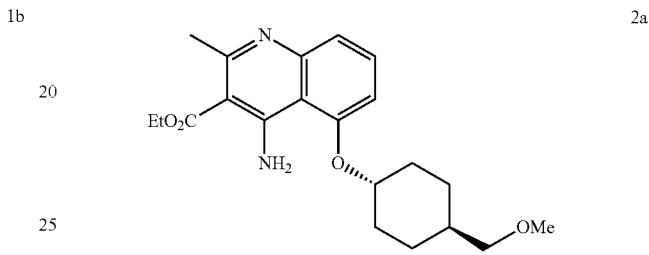

Prepared as in Example 1a from 2-amino-6-((trans-4-(methoxymethyl)cyclohexyl) oxy)benzonitrile (Example 2b) and ethyl acetoacetate. $^1$H NMR (400 MHz, DMSO-d$_6$) δ 8.12 (s, 1H), 7.48 (t, J=8.2 Hz, 1H), 7.19 (dd, J=8.3, 1.0 Hz, 1H), 6.96 (d, 1H), 4.50 (tt, J=10.7, 4.2 Hz, 1H), 4.29 (q, J=7.1 Hz, 2H), 3.20 (s, 4H), 3.13 (d, J=6.3 Hz, 2H), 2.53 (s, 4H), 2.24-2.09 (m, 2H), 1.83-1.71 (m, 2H), 1.65-1.39 (m, 3H), 1.30 (t, J=7.1 Hz, 3H), 1.23-1.00 (m, 2H).

Example 2b

2-Amino-6-((trans-4-(methoxymethyl)cyclohexyl)oxy)benzonitrile

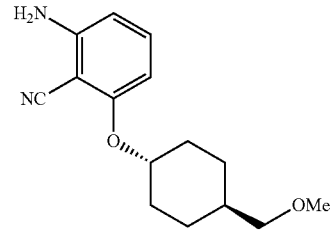

To a solution of 2-((trans-4-(methoxymethyl)cyclohexyl)oxy)-6-nitrobenzonitrile (Example 2c) (1.2 g, 4.1 mmol) in EtOH (20 mL) was added 10% Pd/C (120 mg). The mixture was stirred overnight under a hydrogen atmosphere (balloon), filtered through a bed of celite, washed with EtOH (3×20 mL), and the filtrate was concentrated under reduced pressure, to give 751 mg (69%) of the title product as a yellow solid. $^1$H NMR (400 MHz, DMSO-d$_6$) δ 7.13 (t, J=8.3 Hz, 1H), 6.28 (dd, J=8.4, 0.7 Hz, 1H), 6.24 (dt, J=8.2, 0.7 Hz, 1H), 5.91 (s, 2H), 4.25 (tt, J=10.6, 4.2 Hz, 1H), 3.20 (s, 3H), 3.13 (d, J=6.4 Hz, 2H), 2.07-1.98 (m, 2H), 1.80-1.69 (m, 2H), 1.55 (dddd, J=14.5, 11.5, 5.7, 3.3 Hz, 1H), 1.38-1.27 (m, 2H), 1.17-0.98 (m, 2H).

Example 2c

2-((trans-4-(Methoxymethyl)cyclohexyl)oxy)-6-nitrobenzonitrile

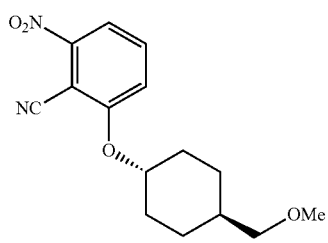

To a solution of trans-4-(methoxymethyl)cyclohexanol (950 mg, 6.6 mmol) in anhydrous THF (30 mL) was added sodium hydride (396 mg, 9.9 mmol, 1.5 equiv., 60% in mineral oil) at 0° C. under nitrogen. The heterogeneous mixture was stirred at 0° C. for 30 min then warm up to room temperature over another 30 min. The mixture was cooled to 0° C., solid 2,6-dinitrobenzonitrile (1.5 g, 7.9 mmol, 1.2 equiv.) was added in one portion and stirred at room temperature overnight. Water was carefully added and extracted with EtOAc (3×50 mL). The combined extract was washed with brine (50 mL), dried over MgSO$_4$, filtered and concentrated under reduced pressure. The residue was purified by silica gel column chromatography (50% EtOAc in hexanes) to afford 1.2 g (62%) of the title compound as a yellow solid. MS 291 (MH$^+$).

Compounds in Table 1 were prepared in a similar manner as described above using alcohols that were either purchased or synthesized following known procedures.

TABLE 1

| Compound | Structure | MS (MH$^+$) |
|---|---|---|
| 102 | | 315 |
| 103 | | 329 |
| 104 | 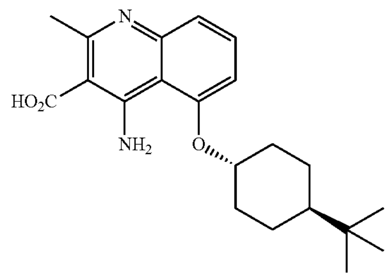 [SMILES: Cc1nc2cccc(O[C@H]3CC[C@H](C(C)(C)C)CC3)c2c(N)c1C(=O)O] | 357 |
| 105 | 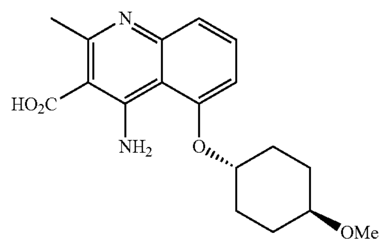 [SMILES: CO[C@H]1CC[C@H](Oc2cccc3nc(C)c(C(=O)O)c(N)c23)CC1] | 331 |
| 106 | 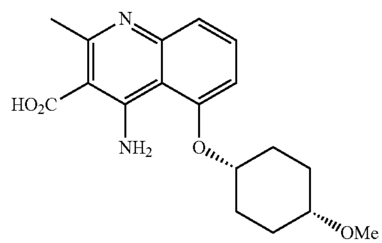 [SMILES: CO[C@H]1CC[C@@H](Oc2cccc3nc(C)c(C(=O)O)c(N)c23)CC1] | 331 |
| 107 | 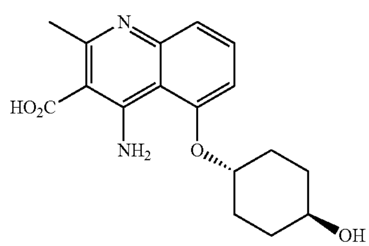 [SMILES: Cc1nc2cccc(O[C@H]3CC[C@H](O)CC3)c2c(N)c1C(=O)O] | 317 |
| 108 | 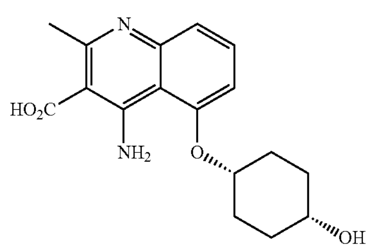 [SMILES: Cc1nc2cccc(O[C@H]3CC[C@@H](O)CC3)c2c(N)c1C(=O)O] | 317 |
| 109 | 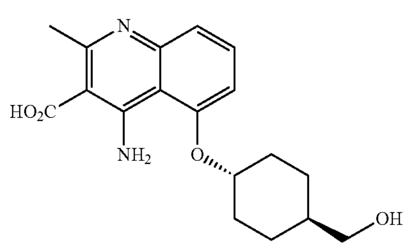 [SMILES: Cc1nc2cccc(O[C@H]3CC[C@H](CO)CC3)c2c(N)c1C(=O)O] | 331 |

Compounds in Table 2 were prepared in a similar manner as described in Examples 1 and 2 using ethyl 3-oxopentanoate or ethyl 3-oxohexanoate instead of ethyl acetoacetate in the cyclization step.

TABLE 2

| Compound | Structure | MS (MH+) |
|---|---|---|
| 200 | 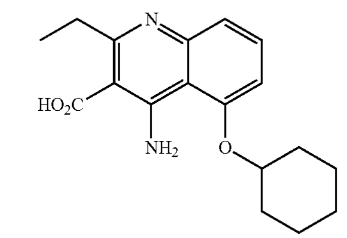 [SMILES: CCc1nc2cccc(OC3CCCCC3)c2c(N)c1C(=O)O] | 315 |
| 201 | 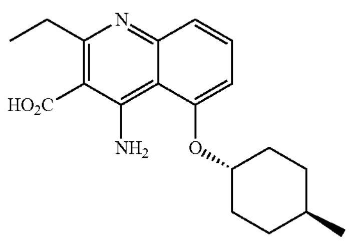 [SMILES: CCc1nc2cccc(O[C@H]3CC[C@H](C)CC3)c2c(N)c1C(=O)O] | 329 |
| 202 | 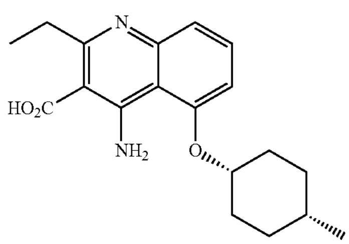 [SMILES: CCc1nc2cccc(O[C@H]3CC[C@@H](C)CC3)c2c(N)c1C(=O)O] | 329 |
| 203 | 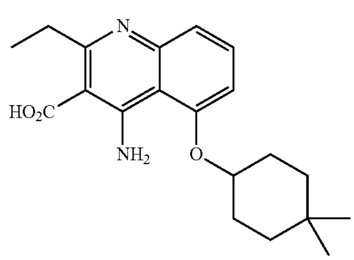 [SMILES: CCc1nc2cccc(OC3CCC(C)(C)CC3)c2c(N)c1C(=O)O] | 343 |
| 204 | | 371 |//

TABLE 2-continued

| Compound | Structure | MS (MH+) |
|---|---|---|
| 205 | 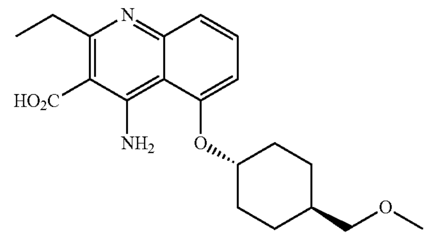 [SMILES: CCc1nc2cccc(O[C@H]3CC[C@H](COC)CC3)c2c(N)c1C(=O)O] | 359 |
| 206 | 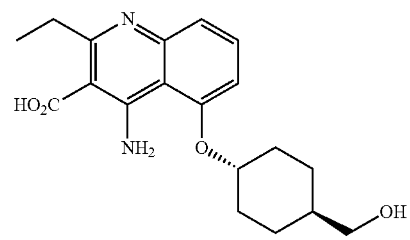 [SMILES: CCc1nc2cccc(O[C@H]3CC[C@H](CO)CC3)c2c(N)c1C(=O)O] | 345 |
| 207 | 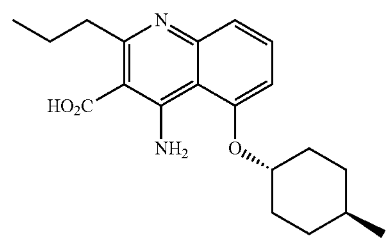 [SMILES: CCCc1nc2cccc(O[C@H]3CC[C@H](C)CC3)c2c(N)c1C(=O)O] | 343 |
| 208 | 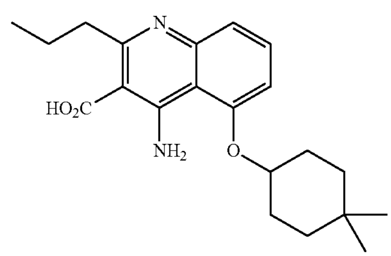 [SMILES: CCCc1nc2cccc(OC3CCC(C)(C)CC3)c2c(N)c1C(=O)O] | 357 |

Example 3

4-Amino-5-((trans-4-(2-ethoxyacetamido)cyclohexyl)oxy)-2-methylquinoline-3-carboxylic acid

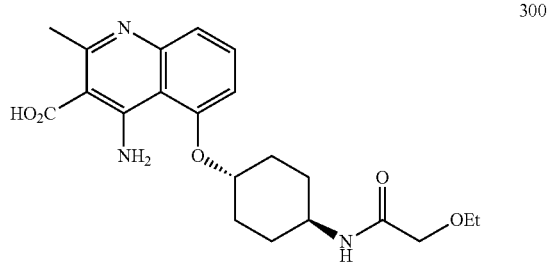 [SMILES: CCOCC(=O)N[C@H]1CC[C@H](Oc2cccc3nc(C)c(C(=O)O)c(N)c23)CC1]

300

Prepared as in Example 1 from ethyl 4-amino-5-((trans-4-(2-ethoxyacetamido) cyclohexyl)oxy)-2-methylquinoline-3-carboxylate (Example 3a) in 29% yield as a white crystalline solid. mp=204-206° C. $^1$H NMR (400 MHz, DMSO-d$_6$) δ 13.03 (br s, 1H), 12.01 (br s, 1H), 8.82 (br s, 1H), 7.68 (t, J=8.2 Hz, 1H), 7.60 (d, J=8.0 Hz, 1H), 7.31 (d, J=8.3 Hz, 1H), 7.16 (d, J=8.3 Hz, 1H), 4.71-4.57 (m, 1H), 3.82 (s, 2H), 3.78-3.62 (m, 1H), 3.48 (q, J=7.0 Hz, 2H), 2.79 (s, 3H), 2.25-2.10 (m, 2H), 1.92-1.78 (m, 2H), 1.77-1.60 (m, 2H), 1.58-1.40 (m, 2H), 1.15 (t, J=7.0 Hz, 3H). MS 402 (MH$^+$).

Example 3a

Ethyl 4-amino-5-((trans-4-(2-ethoxyacetamido)cyclohexyl)oxy)-2-methyl quinoline-3-carboxylate

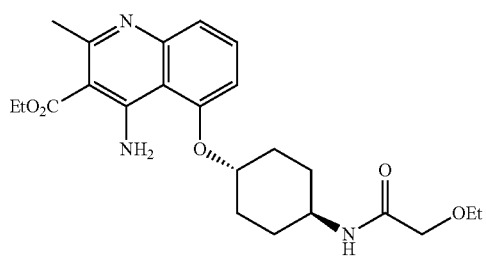

3a

Prepared as in Example 1b from N-(trans-4-(3-amino-2-cyanophenoxy)cyclohexyl)-2-ethoxyacetamide (Example 3b) and ethyl acetoacetate in 79% yield as a pale yellow solid. $^1$H NMR (400 MHz, DMSO-d$_6$) δ 8.13 (br s, 2H), 7.59 (d, J=8.1 Hz, 1H), 7.52 (t, J=8.2 Hz, 1H), 7.23 (d, J=8.3 Hz, 1H), 7.01 (d, J=7.8 Hz, 1H), 4.62-4.50 (m, 1H), 4.32 (q, J=7.0 Hz, 2H), 3.81 (s, 2H), 3.77-3.61 (m, 1H), 3.48 (q, J=6.9 Hz, 2H), 2.56 (s, 3H), 2.26-2.12 (m, 2H), 1.90-1.75 (m, 2H), 1.71-1.56 (m, 2H), 1.56-1.42 (m, 2H), 1.33 (t, J=7.1 Hz, 3H), 1.15 (t, J=7.0 Hz, 3H). MS 430 (MH$^+$).

Example 3b

N-(trans-4-(3-amino-2-cyanophenoxy)cyclohexyl)-2-ethoxyacetamide

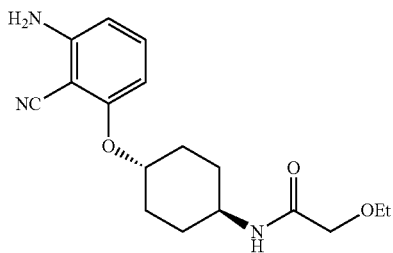

3b

To a solution of 2-ethoxy-N-(trans-4-hydroxycyclohexyl) acetamide (20.10 g, 99.87 mmol) in anhydrous 1,4-dioxane (800 mL), was added portion-wise sodium hydride (4.33 g, 108.25 mmol, 60% in mineral oil) at room temperature under nitrogen. The mixture was stirred for 1 h at room temperature, and then a solution of 2-amino-6-fluorobenzonitrile (11.34 g, 83.30 mmol) in anhydrous 1,4-dioxane (200 mL) was added drop-wise. The reaction mixture was heated at 90° C. over 72 h, cooled to room temperature, concentrated under reduced pressure, ice water (150 mL) was carefully added and extracted with EtOAc (5×200 mL). The combined extract was washed with brine, dried over MgSO$_4$, filtered and the solvent was evaporated. The residue was purified by silica gel column chromatography (35% to 65% EtOAc in hexanes) to afford 18.98 g (72%) of the title compound as a pale yellow solid. $^1$H NMR (400 MHz, CDCl$_3$) δ 7.18 (t, J=8.2 Hz, 1H), 6.44 (d, J=8.2 Hz, 1H), 6.29 (d, J=8.3 Hz, 1H), 6.21 (d, J=8.3 Hz, 1H), 4.39 (br s, 2H), 4.31-4.21 (m, 1H), 4.91 (s, 2H), 3.97-3.84 (m, 1H), 3.57 (q, J=7.0 Hz, 2H), 2.19-2.05 (m, 4H), 1.78-1.63 (m, 2H), 1.44-1.29 (m, 2H), 1.24 (t, J=7.0 Hz, 3H). MS 318 (MH$^+$).

Example 4

4-Amino-2-methyl-5-((trans-4-(2-(neopentyloxy) acetamido)cyclohexyl)oxy) quinoline-3-carboxylic acid

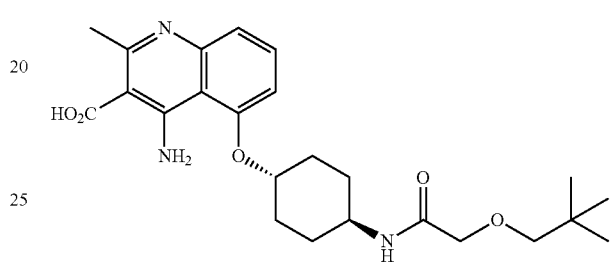

301

To a suspension of 4-amino-5-((trans-4-aminocyclohexyl) oxy)-2-methylquinoline-3-carboxylic acid hydrochloride (Example 5) (315 mg, 1 mmol) and sodium bicarbonate (168 mg, 2 mmol) in DMF (6 mL) and acetonitrile (6 mL) was added a solution of 2-(neopentyloxy)acetic acid (146 mg, 1 mmol), EDCI (192 mg, 1 mmol), and HOBt (135 mg, 1 mmol) in acetonitrile (8 mL) at room temperature. The mixture was stirred at room temperature overnight, concentrated under reduced pressure, diluted with water and acidified with an aqueous 2 M HCl solution to pH-6. The product was isolated by preparative HPLC (RP-C18, water-acetonitrile gradient). The fractions were collected and the solvent was removed under reduced pressure. The residue was co-evaporated with ethanol/water and lyophilized, to give 205 mg (46%) of the title compound as a white solid. $^1$H NMR (400 MHz, DMSO-d$_6$) δ 0.88 (s, 9H), 1.43-1.47 (m, 2H), 1.67-1.70 (m, 2H), 1.84-1.87 (m, 2H), 2.14-2.17 (m, 2H), 2.74 (s, 3H), 3.09 (s, 2H), 3.65-3.71 (m, 1H), 3.82 (s, 2H), 4.63 (m, 1H), 7.13 (d, J=8.4 Hz, 1H), 7.24 (d, J=8.0 Hz, 1H), 7.32 (d, J=8.0 Hz, 1H), 7.65 (t, J=8.0 Hz, 1H). MS 444 (MH$^+$).

Example 5

4-Amino-5-((trans-4-aminocyclohexyl)oxy)-2-methylquinoline-3-carboxylic acid (HCl salt)

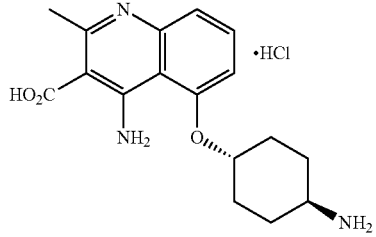

302

To a suspension of ethyl 4-amino-5-((trans-4-(2-ethoxyacetamido)cyclohexyl)oxy)-2-methylquinoline-3-carboxylate (Example 3a) (5.4 g, 12.5 mmol) in EtOH (25 mL) was added an aqueous sodium hydroxide solution (4M, 19 mL, ~6 equiv.) at room temperature. The mixture was heated at 80° C. overnight, cooled to room temperature, ethanol was removed under reduced pressure and the pH was adjusted to 2 with an aqueous 4 M HCl solution. The product was isolated by preparative HPLC (RP-C18, water-acetonitrile gradient). The fractions were collected, the solvent evaporated and the residue was dried under vacuum to afford 3.5 g (88%) of the title product as a yellow solid. $^1$H NMR (400 MHz, DMSO-$d_6$) δ 1.78-1.44 (m, 4H), 2.13-1.98 (m, 2H), 2.31-2.16 (m, 2H), 2.82 (s, 3H), 3.15-2.98 (m, 1H), 4.75-4.60 (m, 1H), 7.28 (d, J=8.2 Hz, 1H), 7.52 (d, J=8.3 Hz, 1H), 7.74 (t, J=8.3 Hz, 1H), 8.33 (br s, 2H), 8.93 (br s, 1H), 11.22 (br s, 1H), 13.57 (br s, 1H). MS 316 (MH$^+$).

Compounds in Table 3 were prepared in a similar manner as described in Example 4 from 4-amino-5-((trans-4-aminocyclohexyl)oxy)-2-methylquinoline-3-carboxylic acid hydrochloride (Example 5) or 4-amino-5-((trans-4-aminocyclohexyl)oxy)-2-ethylquinoline-3-carboxylic acid (prepared in a similar manner as compound 302 using ethyl 3-oxopentanoate instead of ethyl acetoacetate in the cyclization step) and corresponding carboxylic acids that were either commercially available or prepared using known procedures.

TABLE 3

| SID | Structure | MS (MH$^+$) |
|---|---|---|
| 303 | 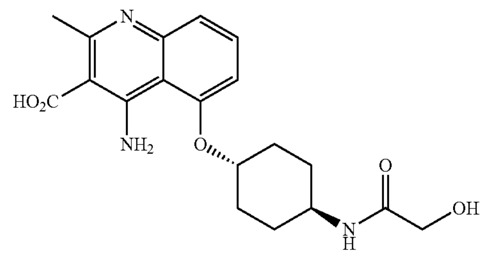 [SMILES: Cc1nc2cccc(O[C@H]3CC[C@H](NC(=O)CO)CC3)c2c(N)c1C(=O)O] | 374 |
| 304 | 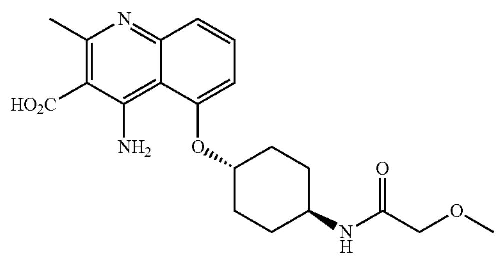 | 388 |
| 305 | 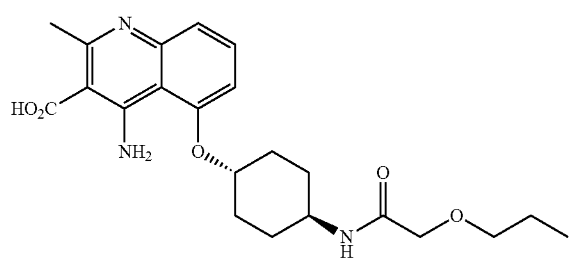 [SMILES: CCCOCC(=O)N[C@H]1CC[C@H](Oc2cccc3nc(C)c(C(=O)O)c(N)c23)CC1] | 416 |
| 306 | 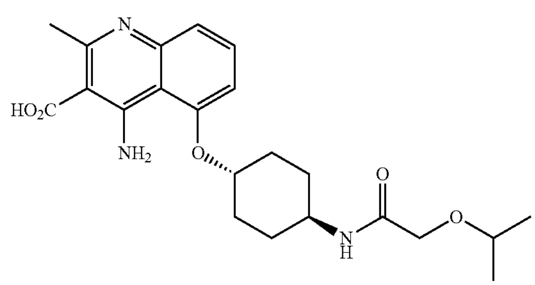 [SMILES: Cc1nc2cccc(O[C@H]3CC[C@H](NC(=O)COC(C)C)CC3)c2c(N)c1C(=O)O] | 416 |

TABLE 3-continued

| SID | Structure | MS (MH+) |
|---|---|---|
| 307 | 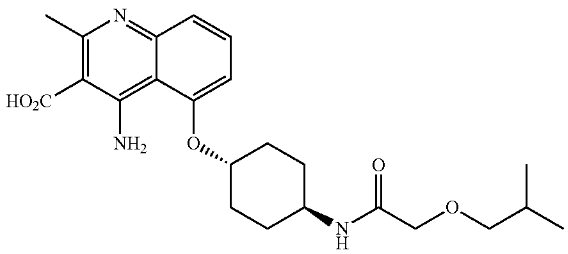 [SMILES: Cc1nc2cccc(O[C@H]3CC[C@H](NC(=O)COCC(C)C)CC3)c2c(N)c1C(=O)O] | 430 |
| 308 | 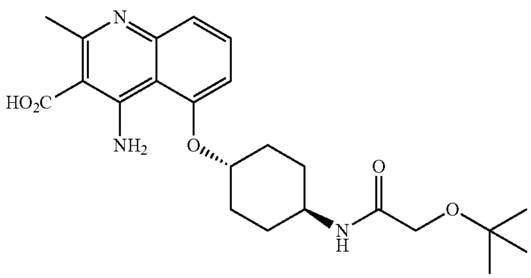 [SMILES: Cc1nc2cccc(O[C@H]3CC[C@H](NC(=O)COC(C)(C)C)CC3)c2c(N)c1C(=O)O] | 430 |
| 309 | 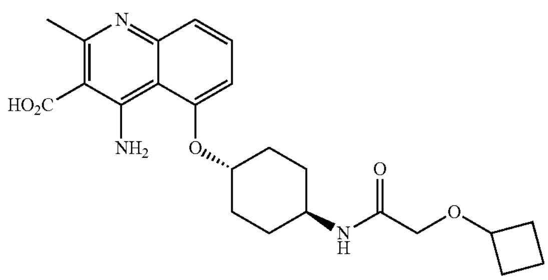 [SMILES: Cc1nc2cccc(O[C@H]3CC[C@H](NC(=O)COC4CCC4)CC3)c2c(N)c1C(=O)O] | 428 |
| 310 | 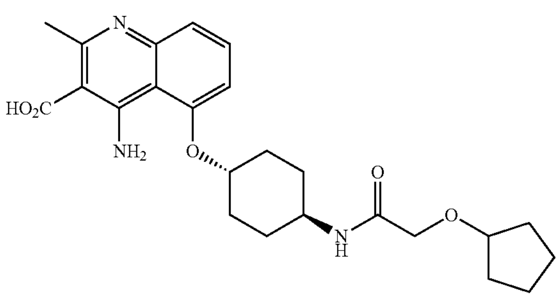 [SMILES: Cc1nc2cccc(O[C@H]3CC[C@H](NC(=O)COC4CCCC4)CC3)c2c(N)c1C(=O)O] | 442 |
| 311 | 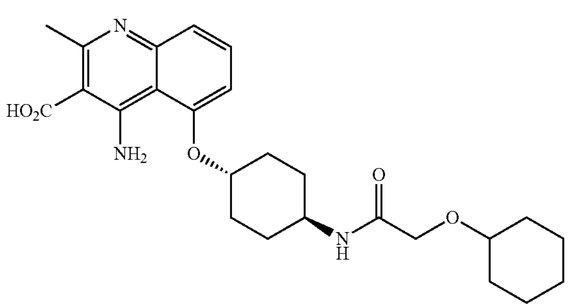 [SMILES: Cc1nc2cccc(O[C@H]3CC[C@H](NC(=O)COC4CCCCC4)CC3)c2c(N)c1C(=O)O] | 456 |

TABLE 3-continued

| SID | Structure | MS (MH+) |
|---|---|---|
| 312 | 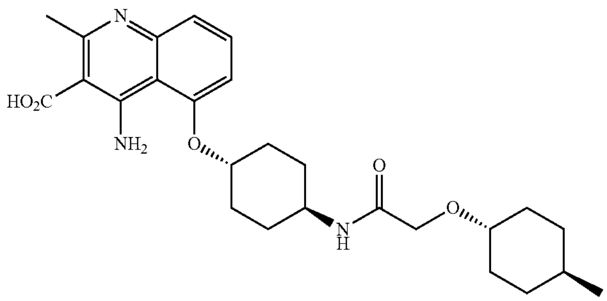 | 470 |
| 313 | 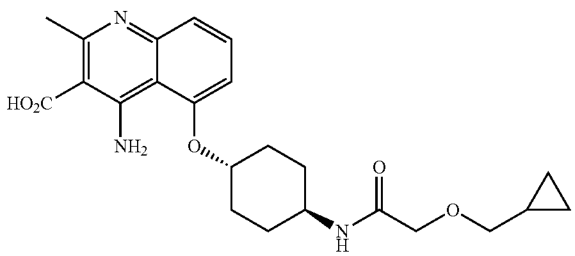 [SMILES: Cc1nc2cccc(O[C@H]3CC[C@H](NC(=O)COCC4CC4)CC3)c2c(N)c1C(=O)O] | 428 |
| 314 | 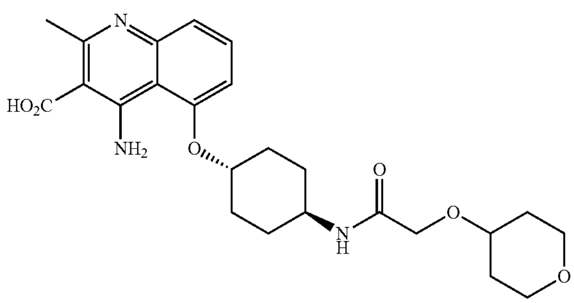 [SMILES: Cc1nc2cccc(O[C@H]3CC[C@H](NC(=O)COC4CCOCC4)CC3)c2c(N)c1C(=O)O] | 458 |
| 315 | 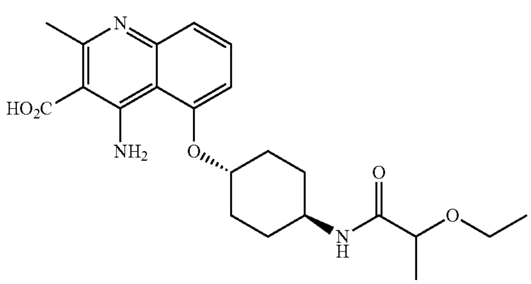 [SMILES: CCOC(C)C(=O)N[C@H]1CC[C@H](Oc2cccc3nc(C)c(C(=O)O)c(N)c23)CC1] | 416 |
| 316 | 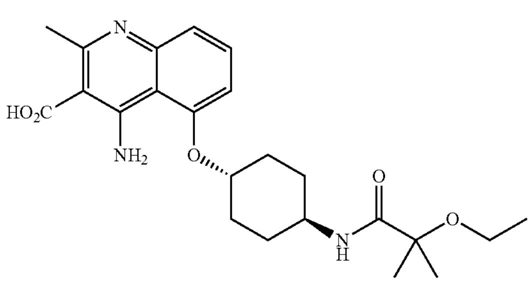 [SMILES: CCOC(C)(C)C(=O)N[C@H]1CC[C@H](Oc2cccc3nc(C)c(C(=O)O)c(N)c23)CC1] | 430 |

TABLE 3-continued

| SID | Structure | MS (MH+) |
|---|---|---|
| 317 | 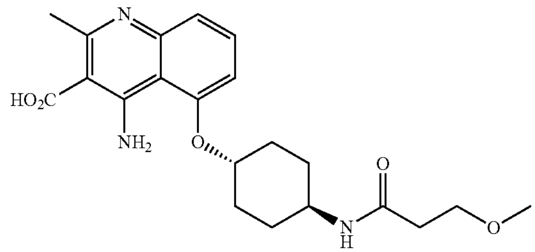 | 402 |
| 318 | 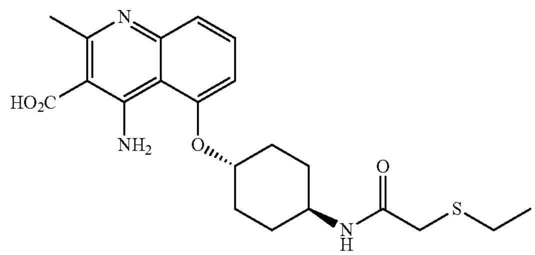 [SMILES: CCSCC(=O)N[C@H]1CC[C@H](Oc2cccc3nc(C)c(C(=O)O)c(N)c23)CC1] | 418 |
| 319 | 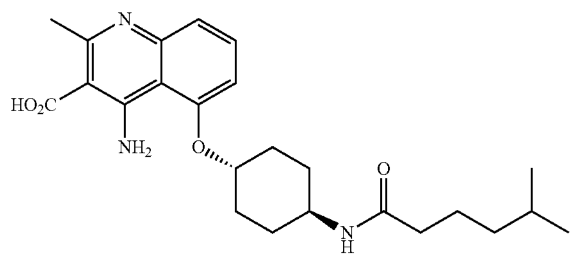 | 428 |
| 320 | 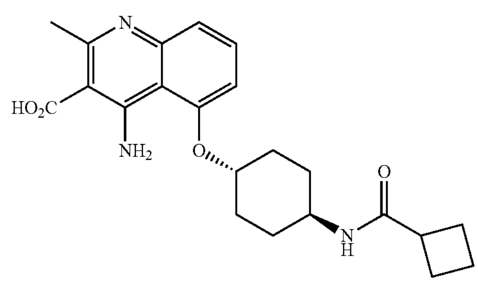 [SMILES: Cc1nc2cccc(O[C@H]3CC[C@H](NC(=O)C4CCC4)CC3)c2c(N)c1C(=O)O] | 398 |
| 321 | 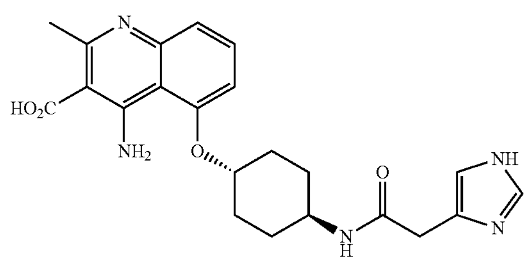 [SMILES: Cc1nc2cccc(O[C@H]3CC[C@H](NC(=O)Cc4c[nH]cn4)CC3)c2c(N)c1C(=O)O] | 424 |
| 322 | 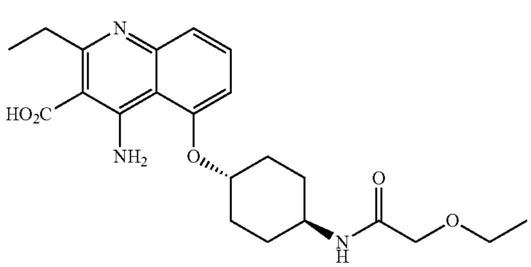 [SMILES: CCOCC(=O)N[C@H]1CC[C@H](Oc2cccc3nc(CC)c(C(=O)O)c(N)c23)CC1] | 416 |

TABLE 3-continued
| SID | Structure | MS (MH+) |
|---|---|---|
| 323 | 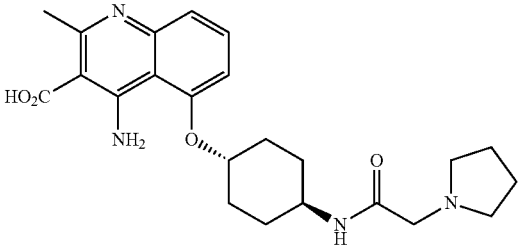 [SMILES: Cc1nc2cccc(O[C@H]3CC[C@H](NC(=O)CN4CCCC4)CC3)c2c(N)c1C(=O)O] | 427 |
| 324 | 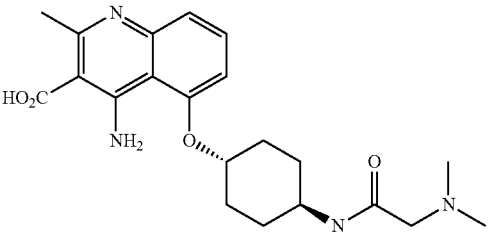 | 401 |
| 325 | 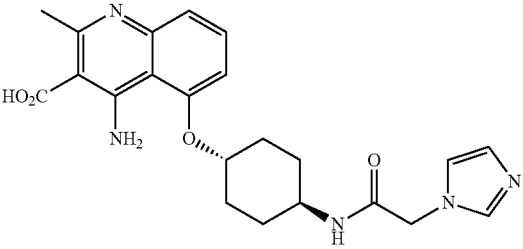 [SMILES: Cc1nc2cccc(O[C@H]3CC[C@H](NC(=O)Cn4ccnc4)CC3)c2c(N)c1C(=O)O] | 424 |
| 326 | 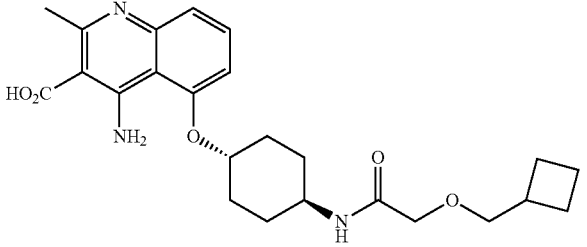 [SMILES: Cc1nc2cccc(O[C@H]3CC[C@H](NC(=O)COCC4CCC4)CC3)c2c(N)c1C(=O)O] | 442 |
| 327 | 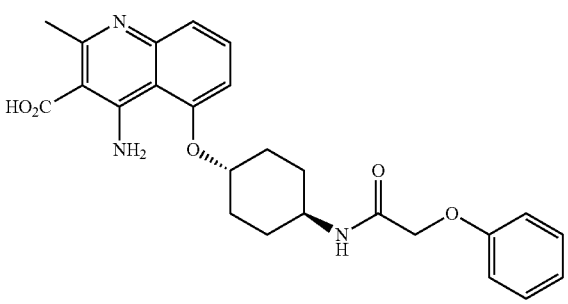 [SMILES: Cc1nc2cccc(O[C@H]3CC[C@H](NC(=O)COc4ccccc4)CC3)c2c(N)c1C(=O)O] | 450 |

TABLE 3-continued

| SID | Structure | MS (MH+) |
|---|---|---|
| 328 | 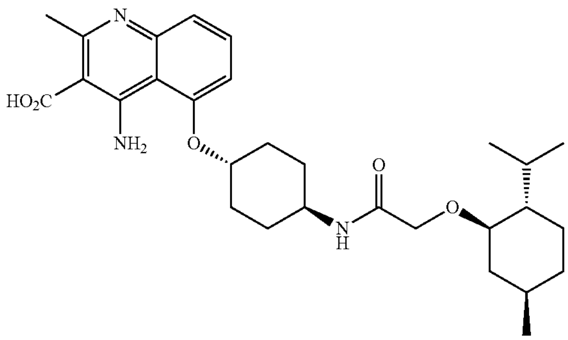 [SMILES: Cc1nc2cccc(O[C@H]3CC[C@H](NC(=O)CO[C@@H]4C[C@H](C)CC[C@H]4C(C)C)CC3)c2c(N)c1C(=O)O] | 512 |
| 329 | 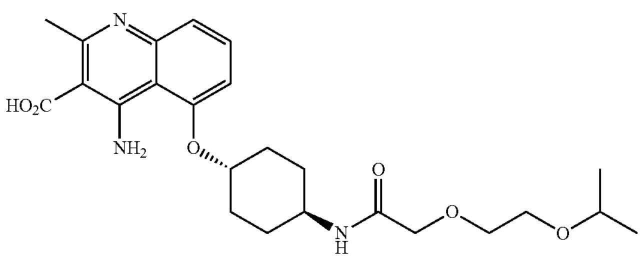 [SMILES: Cc1nc2cccc(O[C@H]3CC[C@H](NC(=O)COCCOC(C)C)CC3)c2c(N)c1C(=O)O] | 460 |
| 330 | 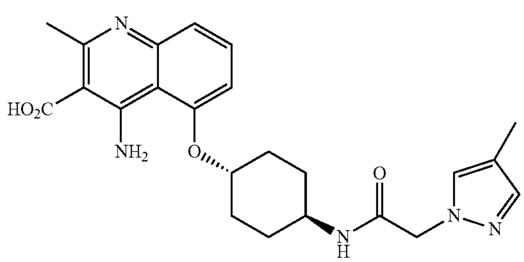 [SMILES: Cc1cnn(CC(=O)N[C@H]2CC[C@H](Oc3cccc4nc(C)c(C(=O)O)c(N)c34)CC2)c1] | 438 |
| 331 | 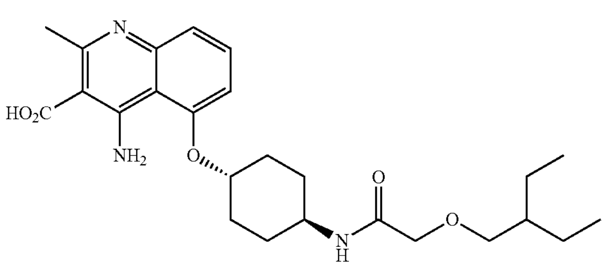 [SMILES: CCC(CC)COCC(=O)N[C@H]1CC[C@H](Oc2cccc3nc(C)c(C(=O)O)c(N)c23)CC1] | 458 |
| 332 | 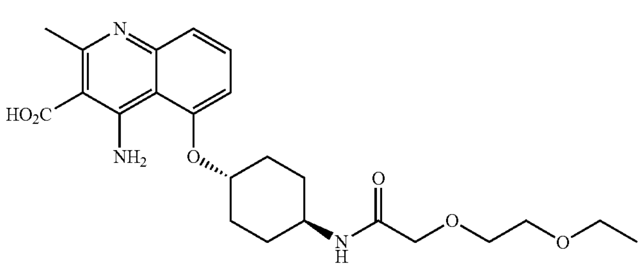 [SMILES: CCOCCOCC(=O)N[C@H]1CC[C@H](Oc2cccc3nc(C)c(C(=O)O)c(N)c23)CC1] | 446 |

TABLE 3-continued

| SID | Structure | MS (MH+) |
|---|---|---|
| 333 | 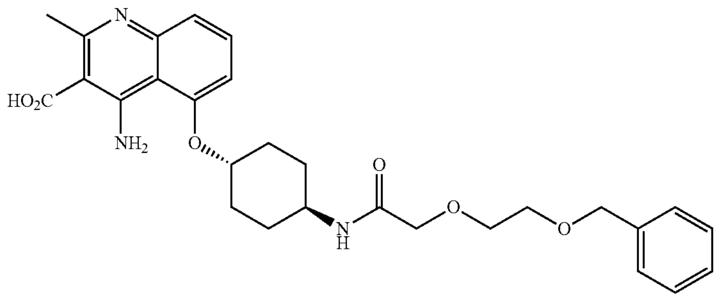 [SMILES: Cc1nc2cccc(O[C@H]3CC[C@H](NC(=O)COCCOCc4ccccc4)CC3)c2c(N)c1C(=O)O] | 508 |
| 334 | 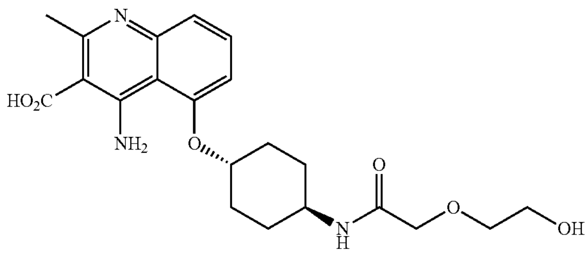 [SMILES: Cc1nc2cccc(O[C@H]3CC[C@H](NC(=O)COCCO)CC3)c2c(N)c1C(=O)O] | 418 |
| 335 | 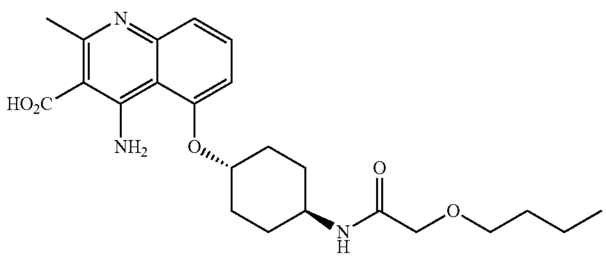 [SMILES: CCCCOCC(=O)N[C@H]1CC[C@H](Oc2cccc3nc(C)c(C(=O)O)c(N)c23)CC1] | 430 |
| 336 | 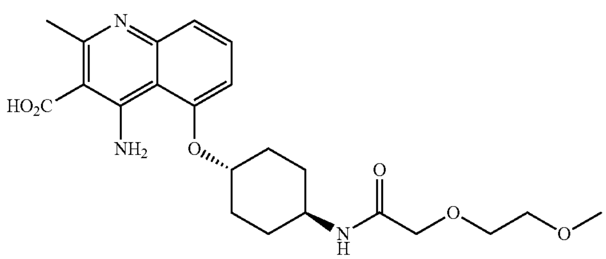 | 432 |
| 337 | 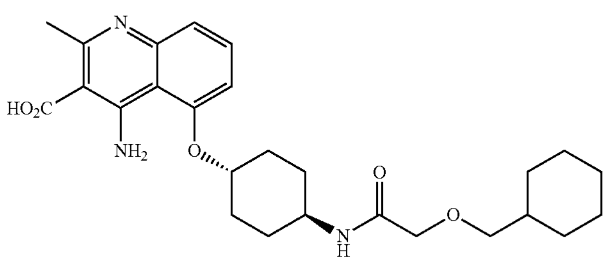 [SMILES: Cc1nc2cccc(O[C@H]3CC[C@H](NC(=O)COCC4CCCCC4)CC3)c2c(N)c1C(=O)O] | 470 |
| 338 | 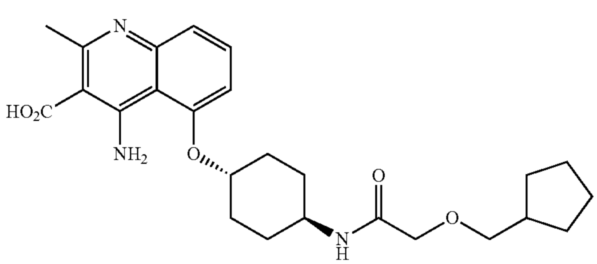 [SMILES: Cc1nc2cccc(O[C@H]3CC[C@H](NC(=O)COCC4CCCC4)CC3)c2c(N)c1C(=O)O] | 456 |

TABLE 3-continued

| SID | Structure | MS (MH+) |
|---|---|---|
| 339 | 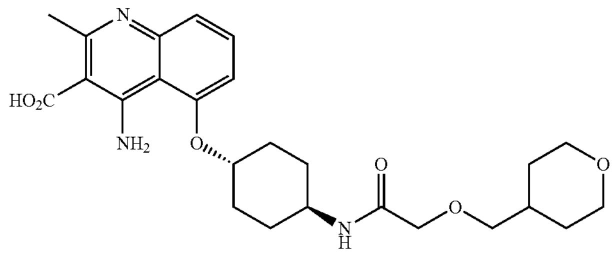 [SMILES: Cc1nc2cccc(O[C@H]3CC[C@H](NC(=O)COCC4CCOCC4)CC3)c2c(N)c1C(=O)O] | 472 |
| 340 | 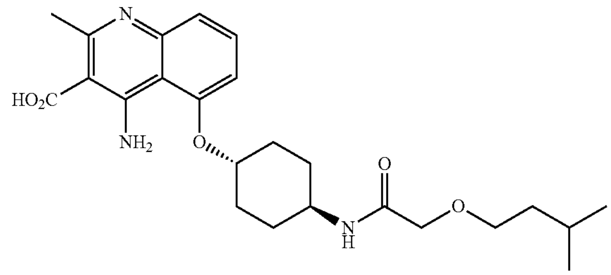 [SMILES: Cc1nc2cccc(O[C@H]3CC[C@H](NC(=O)COCCC(C)C)CC3)c2c(N)c1C(=O)O] | 444 |
| 341 | 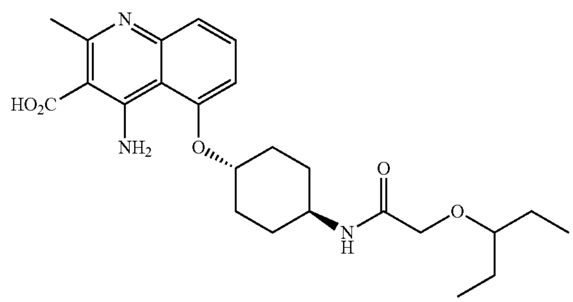 [SMILES: CCC(CC)OCC(=O)N[C@H]1CC[C@H](Oc2cccc3nc(C)c(C(=O)O)c(N)c23)CC1] | 444 |

Example 6

4-Amino-5-((trans-4-(2-(ethylamino)acetamido)cyclohexyl)oxy)-2-methyl quinolone-3-carboxylic acid (HCl)

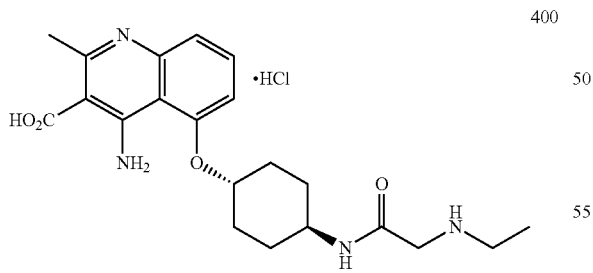

To a solution of 4-amino-5-((trans-4-(2-((tert-butoxycarbonyl)(ethyl)amino)acetamido) cyclohexyl)oxy)-2-methylquinoline-3-carboxylic acid (Example 6a) (475 mg, 0.95 mmol) in MeOH (5 mL) was added concentrated HCl (0.5 mL) at 0° C. The mixture was warmed up and stirred at room temperature overnight. The reaction mixture was diluted with water and the product was isolated by preparative HPLC (RPC-18, water-acetonitrile gradient). The clean fraction was collected, concentrated under reduced pressure and lyophilized, to give 198 mg (51%) of the title compound as a white solid. $^1$H NMR (400 MHz, DMSO-$d_6$) δ 0.99 (t, J=7.2 Hz, 3H), 1.37-1.47 (m, 2H), 1.56-1.65 (m, 2H), 1.83-1.86 (m, 2H), 2.11-2.17 (m, 3H), 2.45-2.51 (m, 2H), 2.57 (s, 3H), 3.04 (s, 2H), 3.64-3.69 (m, 1H), 4.48-4.53 (m, 1H), 6.8 (d, J=8.0 Hz, 1H), 7.13 (d, J=8.0 Hz, 1H), 7.32 (t, J=8.0 Hz, 1H), 7.71-7.73 (m, 1H). MS 401 (MH+).

Example 6a

4-Amino-5-((trans-4-(2-((tert-butoxycarbonyl)(ethyl)amino)acetamido) cyclohexyl)oxy)-2-methylquinoline-3-carboxylic acid

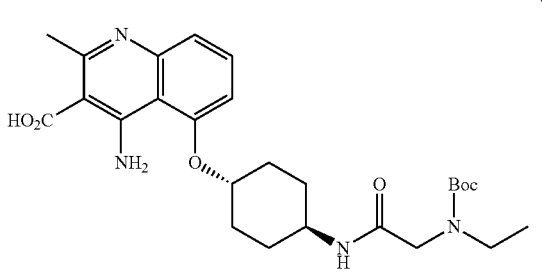

Prepared as in Example 4 from 2-((tert-butoxycarbonyl)(ethyl)amino)acetic acid and 4-amino-5-(trans-4-aminocyclohexyloxy)-2-methylquinoline-3-carboxylic acid hydrochloride (Example 5) in 83% yield as a white solid. MS 501 (MH+).

Compounds in Table 4 were prepared in a similar manner as described in Example 6 from 4-amino-5-(trans-4-aminocyclohexyloxy)-2-methylquinoline-3-carboxylic acid hydrochloride (Example 5) and the corresponding Boc-protected amino acids and were isolated as the hydrochloride salts.

TABLE 4

| SID | Structure | MS (MH+) |
|---|---|---|
| 401 | 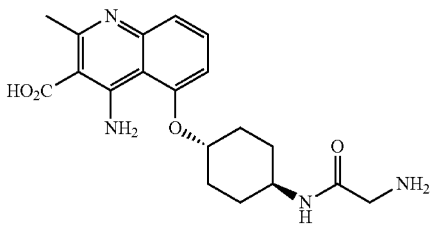 [SMILES: Cc1nc2cccc(O[C@H]3CC[C@H](NC(=O)CN)CC3)c2c(N)c1C(=O)O] | 373 |
| 402 | 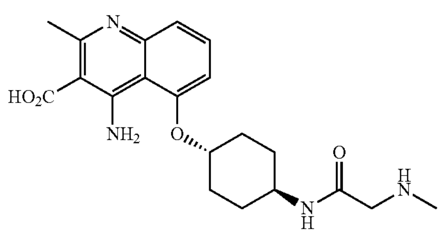 | 387 |

Example 7

4-Amino-2-methyl-5-((trans-4-((S)-2-methylamino)propanamido)cyclohexyl) oxy)quinoline-3-carboxylic acid (HCl)

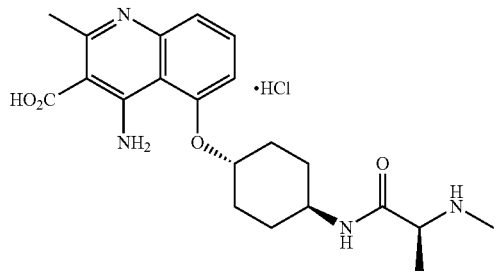

500

To a solution of (S)-2-((tert-butoxycarbonyl)(methyl)amino)propanoic acid (0.064 g, 0.032 mmol) in DMF (1.0 mL) at 0° C. was added HATU (0.145 g, 0.038 mmol, 1.2 equiv.) and the reaction was stirred 1 h. 4-Amino-5-((trans-4-aminocyclohexyl)oxy)-2-methylquinoline-3-carboxylic acid hydrochloride (Example 5) (0.100 g, 0.032 mmol, 1 equiv.) and triethylamine (0.064 g, 0.088 mL, 0.064 mmol, 2 equiv.) were added and the reaction mixture heated at 80° C. for 1 h. Upon cooling to room temperature, the mixture was acidified with an aqueous 4 M HCl solution (2.0 mL) and stirred overnight. The final product was isolated by preparative HPLC (RP-C18, water-acetonitrile gradient). The fractions were collected, the solvent evaporated and the residue was lyophilized to yield 0.050 g (39%) of the product as a white solid. MS 401 (MH+).

Compounds in Table 5 were prepared in a similar manner as described in Example 7 from 4-amino-5-(trans-4-aminocyclohexyloxy)-2-methylquinoline-3-carboxylic acid (Example 5) and the corresponding Boc-protected amino acids and were isolated as the hydrochloride salts.

TABLE 5

| SID | Structure | MS (MH+) |
|---|---|---|
| 501 | 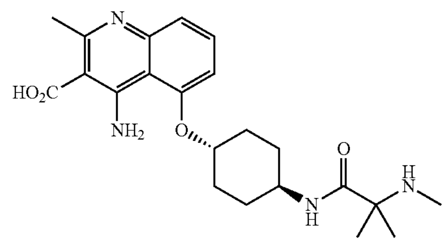 | 415 |
| 502 | 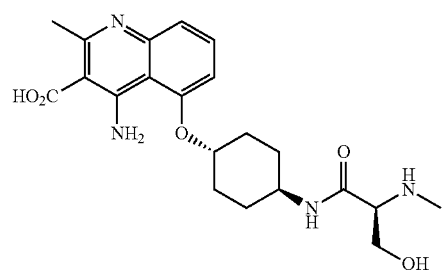 | 417 |
| 503 | 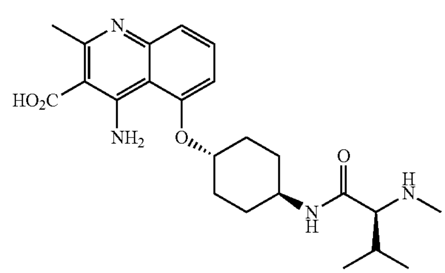 | 429 |
| 504 | 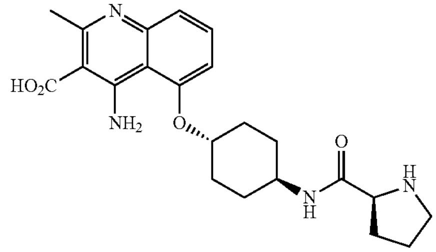 [SMILES: Cc1nc2cccc(O[C@H]3CC[C@H](NC(=O)[C@@H]4CCCN4)CC3)c2c(N)c1C(=O)O] | 413 |

Example 8

4-Amino-2-methyl-5-((trans-4-(2-morpholinoacetamido)cyclohexyl)oxy) quinolone-3-carboxylic acid (HCl)

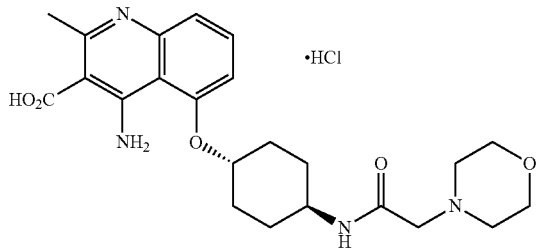

To a mixture of 4-amino-5-((trans)-4-(2-bromoacetamido)cyclohexyloxy)-2-methyl quinolone-3-carboxylic acid (Example 8a) (50 mg, 0.115 mmol) and cesium carbonate (150 mg, 0.46 mmol) in anhydrous DMF (2 mL) was added morpholine (12 mg, 0.136 mmol) at room temperature. The mixture was heated at 80° C. over 4 h, cooled to room temperature diluted with water and pH was adjusted to 2 with an aqueous 2 M HCl solution at 0° C. The product was isolated by preparative HPLC (RP-C18, water-acetonitrile gradient). The fractions were collected and the solvent was removed under reduced pressure. The residue was co-evaporated with ethanol/water and lyophilized, to give 24 mg (47%) of the title compound as a white solid. $^1$H NMR (400 MHz, DMSO-$d_6$) δ 1.57-1.38 (m, 2H), 1.79-1.62 (m, 2H), 1.97-1.80 (m, 2H), 2.26-2.12 (m, 2H), 2.74-2.58 (m, 4H), 2.80 (s, 3H), 3.20 (s, 2H), 3.75-3.62 (m, 5H), 4.80-4.67 (m, 1H), 7.30 (d, J=8.3 Hz, 1H), 7.43 (d, J=8.2 Hz, 1H), 7.80 (t, J=8.3 Hz, 1H), 8.04-7.88 (m, 1H), 9.14 (br s, 1H), 10.60 (br s, 1H), 13.42 (br s, 1H). MS 443 (MH$^+$).

Example 8a

4-Amino-5-((trans-4-(2-bromoacetamido)cyclohexyl)oxy)-2-methyl quinolone-3-carboxylic acid

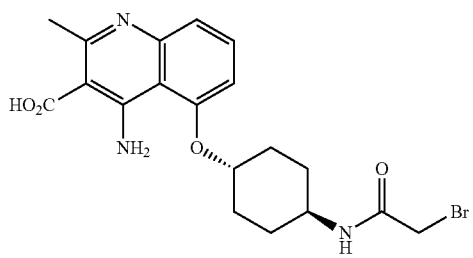

Prepared as in Example 4 from 4-amino-5-((trans-4-aminocyclohexyl)oxy)-2-methyl quinoline-3-carboxylic acid hydrochloride (Example 5) and 2-bromoacetic acid. $^1$H NMR (400 MHz, DMSO-$d_6$) δ 1.56-1.35 (m, 2H), 1.80-1.62 (m, 2H), 1.98-1.82 (m, 2H), 2.26-2.10 (m, 2H), 2.77 (s, 3H), 3.71-3.58 (m, 1H), 4.03 (s, 2H), 4.76-4.58 (m, 1H), 7.19 (d, J=8.3 Hz, 1H), 7.29 (d, J=8.3 Hz, 1H), 7.69 (t, J=8.3 Hz, 1H), 8.22 (d, J=7.6 Hz, 1H), 8.80 (br s, 1H), 11.96 (br s, 1H), 12.82 (br s, 1H). MS 437 (MH$^+$).

Example 9

4-Amino-5-((trans-4-(aminomethyl)cyclohexyl)oxy)-2-methylquinoline-3-carboxylic acid

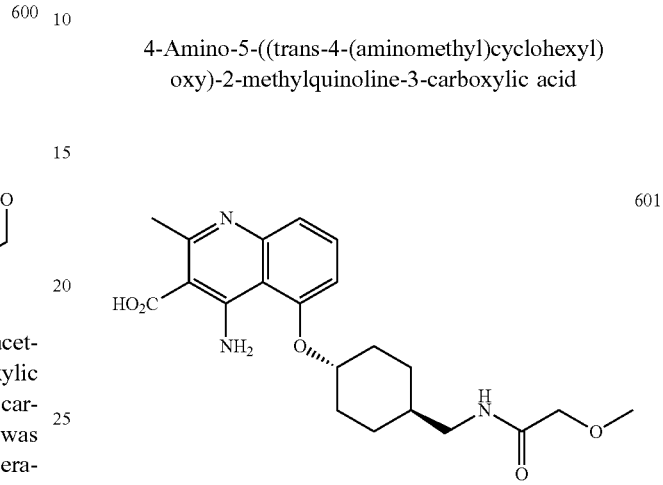

Prepared as in Example 1 from ethyl 4-amino-5-((trans-4-((2-methoxyacetamido) methyl)cyclohexyl)oxy)-2-methylquinoline-3-carboxylate (Example 9a) in 23% yield as a white solid. $^1$H NMR (400 MHz, DMSO-$d_6$) δ 8.69 (s, 1H), 7.83 (t, J=6.0 Hz, 1H), 7.61 (t, J=8.2 Hz, 1H), 7.22 (d, J=8.4 Hz, 1H), 7.09 (d, J=8.2 Hz, 1H), 4.58 (dq, J=8.2, 5.2, 4.0 Hz, 1H), 3.78 (s, 2H), 3.29 (s, 3H), 2.98 (t, J=6.5 Hz, 2H), 2.72 (s, 3H), 2.22-2.11 (m, 2H), 1.80-1.69 (m, 2H), 1.59-1.42 (m, 3H), 1.18-0.99 (m, 2H). MS 402 (MH$^+$).

Example 9a

Ethyl 4-amino-5-((trans-4-((2-methoxyacetamido) methyl)cyclohexyl)oxy)-2-methylquinoline-3-carboxylate

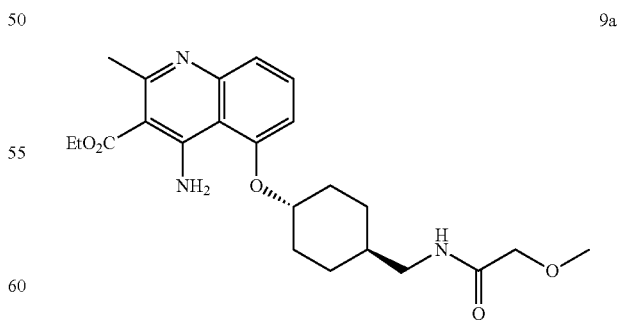

Prepared as in Example 1a from N-((trans-4-(3-amino-2-cyanophenoxy)cyclohexyl) methyl)-2-methoxyacetamide (Example 9b) and ethyl acetoacetate in 55% yield as a yellow solid. MS 430 (MH$^+$).

Example 9b

N-((trans-4-(3-Amino-2-cyanophenoxy)cyclohexyl)methyl)-2-methoxy acetamide

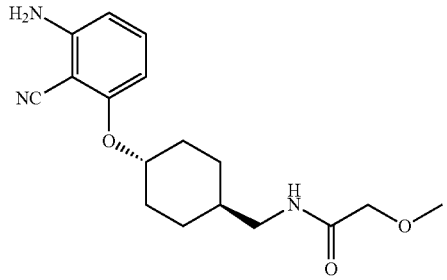

9b

Prepared as in Example 4 from 2-amino-6-((trans-4-(aminomethyl)cyclohexyl)oxy) benzonitrile (Example 9c) and 2-methoxyacetic acid in 98% yield as a colorless oil. $^1$H NMR (400 MHz, DMSO-$d_6$) δ 7.79 (t, J=6.1 Hz, 1H), 7.13 (t, J=8.3 Hz, 1H), 6.28 (dd, J=8.3, 0.7 Hz, 1H), 6.25 (d, J=8.1 Hz, 1H), 5.91 (s, 2H), 4.36-4.16 (m, 1H), 3.77 (s, 2H), 3.28 (s, 3H), 2.98 (t, J=6.8 Hz, 2H), 2.72 (d, J=7.4 Hz, 1H), 2.08-1.96 (m, 2H), 1.75-1.66 (m, 2H), 1.46 (dtd, J=11.1, 7.8, 7.2, 4.0 Hz, 1H), 1.38-1.22 (m, 2H), 1.10-0.90 (m, 2H). MS 318 (MH$^+$).

Example 9c

2-Amino-6-((trans-4-(aminomethyl)cyclohexyl)oxy) benzonitrile

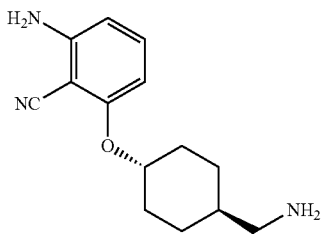

9c

Prepared as in Example 2b from benzyl ((trans-4-(2-cyano-3-nitrophenoxy)cyclohexyl) methyl) carbamate (Example 9d) in quantitative yield as a colorless oil. $^1$H NMR (400 MHz, DMSO-$d_6$) δ 7.14 (t, J=8.2 Hz, 1H), 6.28 (d, J=8.4 Hz, 1H), 6.24 (d, J=8.2 Hz, 1H), 5.92 (s, 2H), 4.25 (tt, J=10.4, 4.4 Hz, 1H), 3.51-3.35 (m, 1H), 2.45-2.24 (m, 2H), 2.15-1.94 (m, 2H), 1.94-1.66 (m, 3H), 1.50-1.14 (m, 3H), 1.14-0.69 (m, 4H). MS 246 (MH$^+$).

Example 9d

Benzyl ((trans-4-(2-cyano-3-nitrophenoxy)cyclohexyl)methyl)carbamate

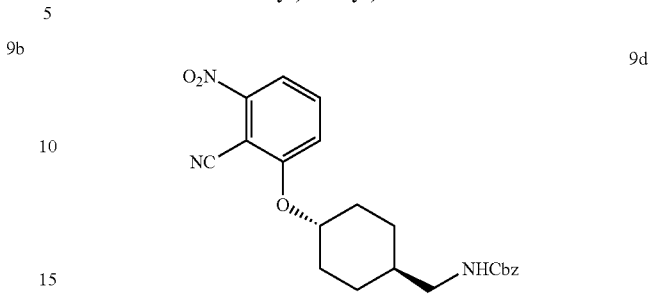

9d

Prepared as in Example 2c from benzyl ((trans-4-hydroxycyclohexyl)methyl)carbamate and 2,6-dinitrobenzonitrile in 99% yield as a yellow solid. $^1$H NMR (400 MHz, DMSO-$d_6$) δ 7.97-7.75 (m, 3H), 7.47-7.16 (m, 5H), 5.00 (s, 2H), 4.70-4.45 (m, 1H), 2.89 (t, J=6.4 Hz, 2H), 2.08 (dd, J=11.8, 4.2 Hz, 2H), 1.85-1.63 (m, 2H), 1.56-1.28 (m, 3H), 1.22-0.93 (m, 2H). MS 410 (MH$^+$).

Example 10

4-Amino-5-((trans-4-((2-methoxyacetamido)methyl)cyclohexyl)oxy)-2-methyl quinoline-3-carboxylic acid (HCl)

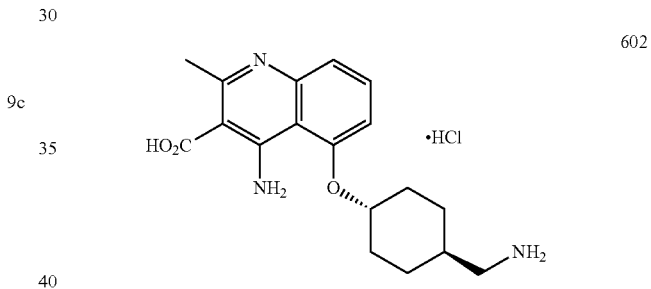

602

Compound 602 was isolated as the hydrochloride salt from the reaction described in Example 9 in 51% yield as a white solid. $^1$H NMR (400 MHz, DMSO-$d_6$) δ 9.85 (s, 1H), 9.27 (s, 1H), 8.45-8.26 (m, 3H), 7.86-7.69 (m, 2H), 7.31 (d, J=7.8 Hz, 1H), 4.70 (dq, J=10.5, 5.9, 5.2 Hz, 1H), 2.84 (s, 3H), 2.73-2.59 (m, 2H), 2.26-2.12 (m, 2H), 2.01-1.85 (m, 2H), 1.79-1.65 (m, 1H), 1.65-1.48 (m, 2H), 1.26-1.04 (m, 2H). MS 330 (MH$^+$).

Compounds in Table 6 were prepared in a similar manner as described in Example 9.

TABLE 6

| SID | Structure | MS (MH$^+$) |
|---|---|---|
| 603 | 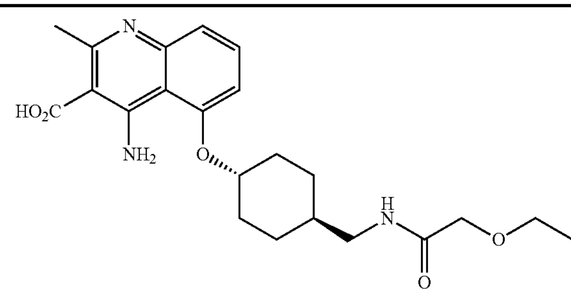 | 416 |

Example 11

4-Amino-2-methyl-5-((trans-4-(pyrimidin-2-ylamino)cyclohexyl)oxy) quinolone-3-carboxylic acid

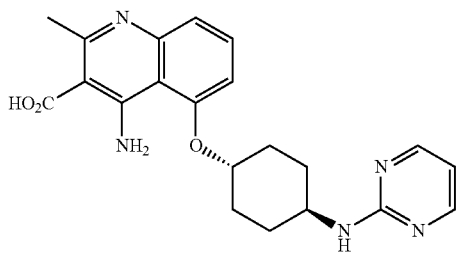

700

Prepared as in Example 1 from ethyl 4-amino-2-methyl-5-((trans-4-(pyrimidin-2-ylamino)cyclohexyl)oxy)quinoline-3-carboxylate (Example 11a) in 55% yield as a white solid. $^1$H NMR (400 MHz, DMSO-$d_6$) δ 1.41-1.58 (m, 2H), 1.64-1.80 (m, 2H), 1.94-2.06 (m, 2H), 2.15-2.28 (m, 2H), 2.77 (s, 3H), 3.70-3.90 (m, 1H), 3.62-3.77 (m, 1H), 6.54 (t, J=4.8 Hz, 1H), 7.12-7.24 (m, 2H), 7.28 (d, J=8.4 Hz, 1H), 7.68 (t, J=8.4 Hz, 1H), 7.26 (d, J=4.8 Hz, 2H), 8.55-8.21 (br s, 1H), 11.75-12.44 (br s, 1H), 12.51-13.08 (br s, 1H). MS 394 (MH$^+$).

Example 11a

Ethyl 4-amino-2-methyl-5-((trans-4-(pyrimidin-2-ylamino)cyclohexyl) oxy)quinoline-3-carboxylate

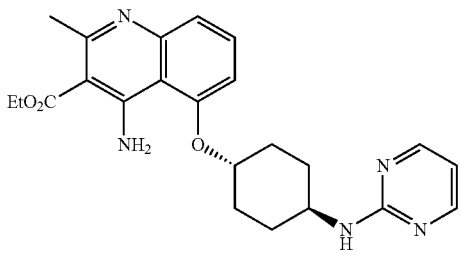

11a

Prepared in a similar manner as in Example 1a from 2-amino-6-((trans-4-(pyrimidin-2-ylamino)cyclohexyl)oxy)benzonitrile (Example 11 b) and ethyl acetoacetate in 15% yield as a beige solid. MS 422 (MH$^+$).

Example 11b

2-Amino-6-((trans-4-(pyrimidin-2-ylamino)cyclohexyl)oxy)benzonitrile

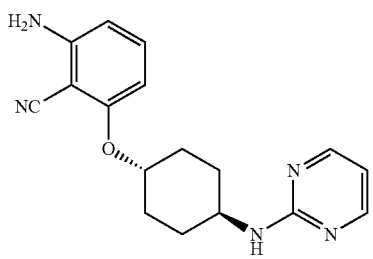

11b

To a solution of trans-4-(pyrimidin-2-ylamino)cyclohexanol (2.0 g, 10.35 mmol,) in anhydrous 1,4-dioxane (225 mL), was added potassium tert-butoxide (1.28 g, 11.39 mmol, 1.1 equiv.) at room temperature under nitrogen. The reaction mixture was stirred at room temperature for 1 h, and a solution of 2-amino-6-fluorobenzonitrile (1.28 g, 9.41 mmol) in anhydrous 1,4-dioxane (25 mL) was added slowly. The mixture was heated gradually to reflux and stirred for 2 h. The reaction was then cooled to room temperature, treated with saturated bicarbonate and extracted with EtOAc. The organic layer was washed with brine, dried over Na$_2$SO$_4$ and purified by chromatography on silica gel to yield the desired product as yellowish solid (2.06 g, 71%). MS 310 (MH$^+$).

Example 12

4-Amino-2-methyl-5-((trans-4-(pyridin-2-ylamino)cyclohexyl)oxy) quinoline-3-carboxylic acid

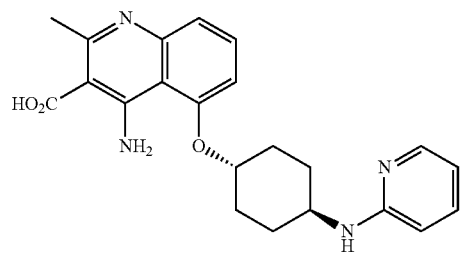

701

Prepared as in Example 1 from ethyl 4-amino-2-methyl-5-((trans-4-(pyridin-2-ylamino)cyclohexyl)oxy)quinoline-3-carboxylate (Example 12a) in 56% yield as a yellow solid $^1$H NMR (400 MHz, DMSO-$d_6$) δ 1.41-1.58 (m, 2H), 1.64-1.80 (m, 2H), 1.94-2.06 (m, 2H), 2.15-2.28 (m, 2H), 2.77 (s, 3H), 3.70-3.90 (m, 1H), 3.62-3.77 (m, 1H), 6.54 (t, J=4.8 Hz, 1H), 7.12-7.24 (m, 2H), 7.28 (d, J=8.4 Hz, 1H), 7.68 (t, J=8.4 Hz, 1H), 7.26 (d, J=4.8 Hz, 2H), 8.55-8.21 (br s, 1H), 11.75-12.44 (br s, 1H), 12.51-13.08 (br s, 1H). MS 394 (MH$^+$).

Example 12a

Ethyl 4-amino-2-methyl-5-((trans-4-(pyridin-2-ylamino)cyclohexyl)oxy) quinoline-3-carboxylate

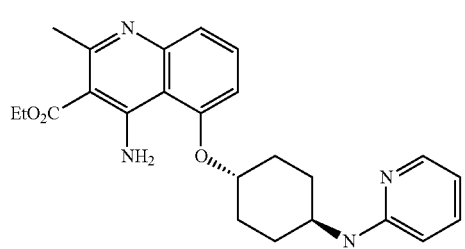

12a

Prepared as in Example 1a from 2-amino-6-((trans-4-(pyridin-2-ylamino)cyclohexyl) oxy)benzonitrile (Example 12b) and ethyl acetoacetate in 41% yield as a yellow solid. MS 421 (MH$^+$).

Example 12b

2-Amino-6-((trans-4-(pyridin-2-ylamino)cyclohexyl) oxy)benzonitrile

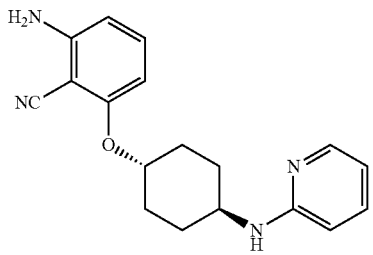

12b

Prepared as in Example 2b from 2-nitro-6-((trans-4-(pyridin-2-ylamino)cyclohexyl) oxy)benzonitrile to give the title compound as a yellow solid. MS 309 (MH$^+$).

Example 12c

2-Nitro-6-((trans-4-(pyridin-2-ylamino)cyclohexyl) oxy)benzonitrile

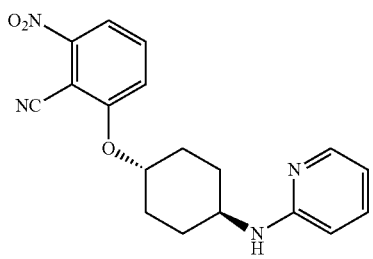

12c

Prepared as in Example 2c from trans-4-(pyridin-2-ylamino)cyclohexanol (1.13 g, 5.89 mmol) and 2,6-dinitrobenzonitrile (1.14 g, 5.89 mmol). The reaction mixture was used in the next step without further purification. MS 339 (MH$^+$).

Example 13

4-Amino-5-((trans-4-((4,6-dimethylpyrimidin-2-yl) amino)cyclohexyl)oxy)-2-methylquinoline-3-carboxylic (HCl)

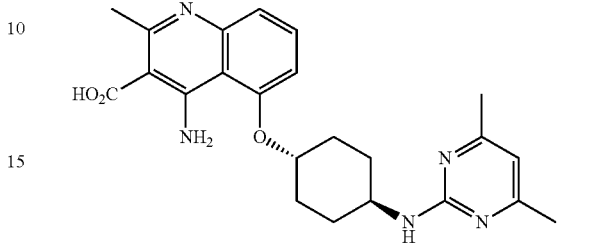

702

To a solution of with 4-amino-5-((trans-4-aminocyclohexyl)oxy)-2-methylquinoline-3-carboxylic acid hydrochloride (Example 5) (50 mg, 0.16 mmol) and K$_2$CO$_3$ (66 mg, 0.48 mmol) in water (1 mL) was added 2-chloro-4,6-dimethylpyrimidine (68 mg, 0.48 mmol). The mixture was heated at 100° C. for 48 hours. Water (1 mL) was added and the mixture was acidified with 3N HCl, and isolated by mass trigger HPLC (water/ACN). The product fractions were combined and concentrated down to furnish the title compound as a brown solid. $^1$H NMR (400 MHz, DMSO-d$_6$) δ 1.55-1.61 (m, 2H), 1.74-1.83 (m, 2H), 2.01-2.03 (m, 2H), 2.21-2.24 (m, 2H), 2.36 (br s, 6H), 2.83 (s, 3H), 4.02 (m, 2H), 4.86 (m, 1H), 6.66 (s, 1H), 7.42 (d, J=8.2 Hz, 1H), 7.58 (d, J=8.4 Hz, 1H), 7.86 (t, J=8.3 Hz, 1H), 9.34 (s, 1H), 9.87 (s, 1H), 14.01 (br s, 1H). MS (MH$^+$) 422.

Compounds in Table 7 were prepared in a similar manner as described in Example 13 from 4-amino-5-((trans-4-aminocyclohexyl)oxy)-2-methylquinoline-3-carboxylic acid hydrochloride (Example 5) and the corresponding substituted 2-chloro-pyrimidine, substituted 4-chloro-pyrimidine or substituted 2-chloropyrazine and were isolated as the hydrochloride salts.

TABLE 7

| SID | Structure | MS (MH$^+$) |
|---|---|---|
| 703 | 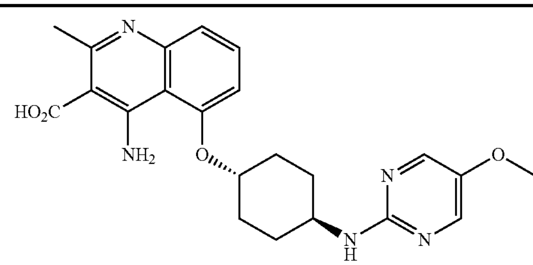 | 424 |
| 704 | 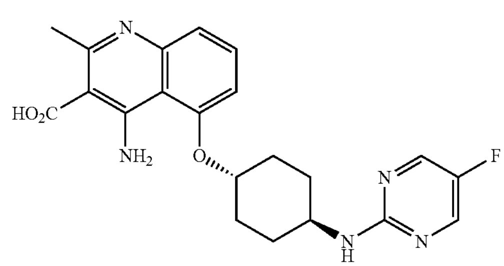 [SMILES: Cc1nc2cccc(O[C@H]3CC[C@H](Nc4ncc(F)cn4)CC3)c2c(N)c1C(=O)O] | 412 |

TABLE 7-continued

| SID | Structure | MS (MH+) |
|---|---|---|
| 705 | 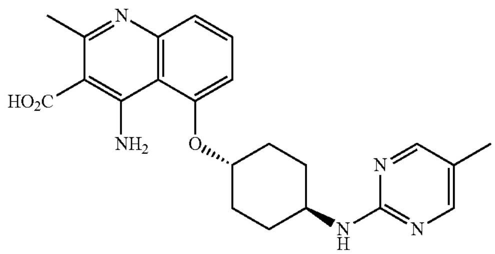 | 408 |
| 706 | 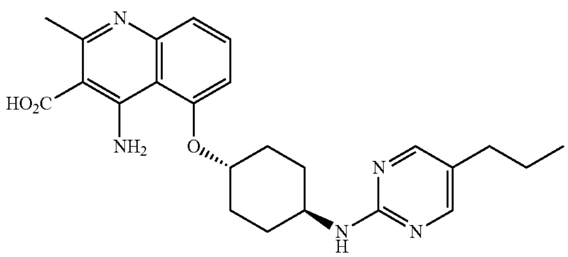 [SMILES: CCCc1cnc(N[C@H]2CC[C@H](Oc3cccc4nc(C)c(C(=O)O)c(N)c34)CC2)nc1] | 436 |
| 707 | 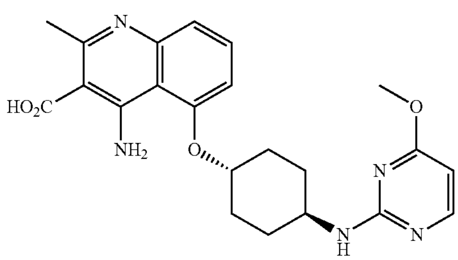 [SMILES: COc1ccnc(N[C@H]2CC[C@H](Oc3cccc4nc(C)c(C(=O)O)c(N)c34)CC2)n1] | 424 |
| 708 | 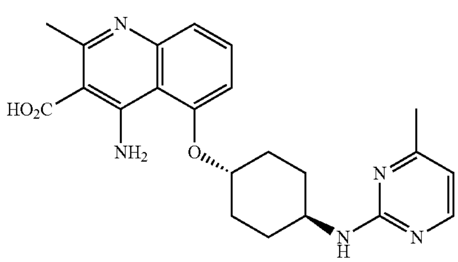 [SMILES: Cc1ccnc(N[C@H]2CC[C@H](Oc3cccc4nc(C)c(C(=O)O)c(N)c34)CC2)n1] | 408 |
| 709 | 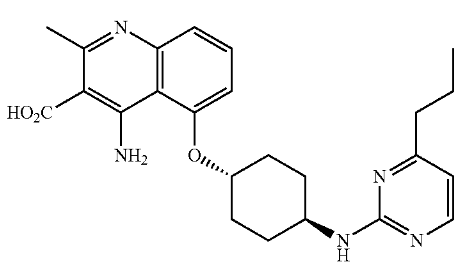 [SMILES: CCCc1ccnc(N[C@H]2CC[C@H](Oc3cccc4nc(C)c(C(=O)O)c(N)c34)CC2)n1] | 436 |
| 710 | 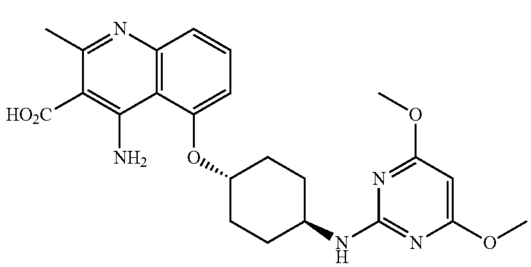 | 454 |

TABLE 7-continued

| SID | Structure | MS (MH+) |
|---|---|---|
| 711 | 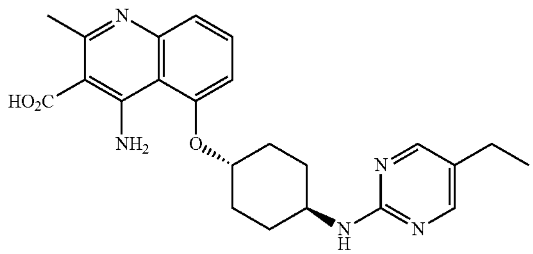 [SMILES: CCc1cnc(N[C@H]2CC[C@H](Oc3cccc4nc(C)c(C(=O)O)c(N)c34)CC2)nc1] | 422 |
| 712 | 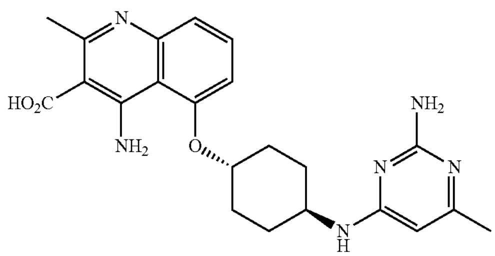 | 423 |
| 713 | 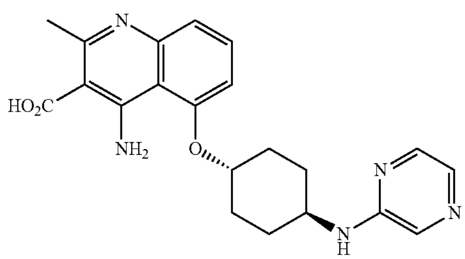 [SMILES: Cc1nc2cccc(O[C@H]3CC[C@H](Nc4cnccn4)CC3)c2c(N)c1C(=O)O] | 394 |
| 714 | 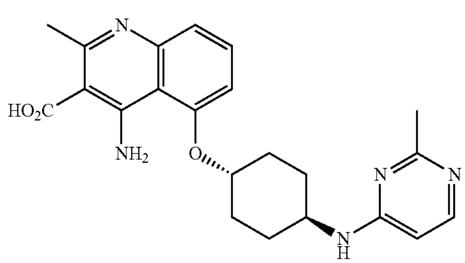 [SMILES: Cc1nccc(N[C@H]2CC[C@H](Oc3cccc4nc(C)c(C(=O)O)c(N)c34)CC2)n1] | 408 |

BIOLOGICAL EXAMPLES

Example 1

Receptor-Based Assay

Potencies ($EC_{50}$ values) for the sweeteners sucrose, sucralose, and fructose were measured against the T1R2/T1R3 taste receptor. $EC_{50}$ was determined using the sweetener alone and in the presence of 1 μM, 3 μM, 10 μM, or 50 μM of test compound. $EC_{50}$ ratios were calculated by the ratio of potency with and without the test compound. The results are presented in Table 8. An "A" value indicates an enhancement ratio of greater than 1 and less than 10. A "B" value indicates an enhancement ratio from 10 to 20. A "C" value indicates an enhancement ratio greater than 20.

TABLE 8

| | Sucrose Enhancement $EC_{50}$ Ratio | | | Sucralose Enhancement $EC_{50}$ Ratio | | Fructose Enhancement $EC_{50}$ Ratio | |
|---|---|---|---|---|---|---|---|
| Compound | 1 μM | 3 μM | 10 μM | 3 μM | 10 μM | 10 μM | 50 μM |
| 100 | B | C | C | | | | |
| 101 | C | C | C | | C | | A |
| 102 | A | A | B | | | | |
| 103 | C | C | | | | | |
| 104 | A | C | | | | | |
| 105 | A | A | C | | | | |
| 106 | A | A | A | | | | |
| 107 | A | A | B | | | | |
| 108 | A | A | A | | | | |
| 109 | B | C | C | | | | |
| 200 | A | A | A | | | | |

TABLE 8-continued

| Compound | Sucrose Enhancement EC$_{50}$ Ratio | | | Sucralose Enhancement EC$_{50}$ Ratio | | Fructose Enhancement EC$_{50}$ Ratio | |
|---|---|---|---|---|---|---|---|
| | 1 μM | 3 μM | 10 μM | 3 μM | 10 μM | 10 μM | 50 μM |
| 201 | A | B | | | | | |
| 202 | A | A | A | | | | |
| 203 | A | A | B | | | | |
| 204 | A | A | A | | | | |
| 205 | A | B | B | B | | | |
| 206 | A | A | A | | | | |
| 207 | A | A | A | | | | |
| 208 | A | A | A | | | | |
| 300 | B | C | C | | B | | |
| 301 | B | B | | B | | | |
| 302 | A | A | | | | | |
| 303 | A | A | B | | A | | |
| 304 | A | B | A | | | | |
| 305 | B | A | A | | C | | |
| 306 | B | A | A | | A | | |
| 307 | A | C | | B | | | |
| 308 | B | | | | | | |
| 309 | B | A | B | B | B | A | |
| 310 | C | | | B | A | A | |
| 311 | B | A | | A | | | |
| 312 | A | A | B | | | | |
| 313 | A | C | A | | | | |
| 314 | B | | | B | | | |
| 315 | B | B | C | | | | |
| 316 | A | A | B | | | | |
| 317 | A | A | B | | | | |
| 318 | A | A | B | B | | A | |
| 319 | A | A | A | | | | |
| 320 | A | B | B | B | | | |
| 321 | A | A | | | | | |
| 322 | A | A | | | | | |
| 323 | A | A | | | | | |
| 324 | A | A | | A | | | |
| 325 | A | B | | A | | | |
| 326 | B | | | | | | |
| 327 | A | | | | | | |
| 328 | A | A | C | | | | |
| 329 | A | B | | A | | | |
| 330 | A | A | A | | | | |
| 331 | A | A | C | | | | |
| 332 | A | B | | | | | |
| 333 | A | B | | | | | |
| 334 | A | A | C | | A | | |
| 335 | B | C | | C | | | |
| 336 | A | C | | B | | | |
| 337 | A | C | | | | | |
| 338 | A | | | | | | |
| 339 | A | B | | | | | |
| 340 | B | B | | A | | | |
| 341 | A | B | | A | | | |
| 400 | A | A | A | A | A | A | |
| 401 | A | A | A | A | A | | |
| 402 | A | A | B | A | A | | |
| 500 | A | A | A | A | | A | |
| 501 | A | A | A | B | A | A | |
| 502 | A | A | A | A | A | A | |
| 503 | A | A | A | B | A | A | |
| 504 | A | A | | | | | |
| 600 | B | C | | | | | |
| 601 | A | C | C | | A | | |
| 602 | A | A | C | | A | | |
| 603 | A | C | C | C | | | |
| 700 | A | C | C | C | C | | |
| 701 | A | B | B | C | C | | |
| 702 | A | A | A | A | B | | |
| 703 | A | A | B | B | B | A | |
| 704 | A | A | B | B | B | A | A |
| 705 | A | B | A | A | B | A | |
| 706 | A | A | B | A | B | A | A |
| 707 | A | A | B | A | B | A | A |
| 708 | A | C | C | C | C | A | |
| 709 | A | A | A | A | A | | |
| 710 | A | A | B | A | B | A | A |
| 711 | A | A | B | B | B | A | A |
| 712 | A | B | C | B | C | A | A |
| 713 | A | B | B | A | B | A | A |
| 714 | A | A | A | A | A | A | A |

Example 2

Sensory Experiments

Test samples containing either a sweetener (sucrose or high-fructose corn syrup) alone or in combination with a test compound were presented in pairs to a group of panelist who were asked to determine which of the samples was sweeter. Subjects refrained from eating or drinking (except water) for at least 1 hour prior to the test. Subjects rinsed with water several times to clean the mouth. The samples within a paired comparison test were presented in a randomized, counterbalanced order. Panelists had up to a 1 minute delay between taste tests to clear the mouth of any tastes. Binomial probability tables were used to determine the probability of the correct number of responses occurring for each test at alpha-0.05.

Stock solutions of test compounds were prepared at 1000× final concentration with ethanol to ensure dispersion in solution. Test compound samples including sucrose were prepared by diluting the stock solutions in a low sodium buffer (0.952 g of KCl, 5.444 g of $Na_2HPO_4$, and 0.952 g of $KH_2PO_4$ in deionized ultrafiltered water) at pH 7.1 and containing sucrose. Test compound samples including high fructose corn syrup were prepared by diluting the stock solutions in the low sodium buffer at pH 2.8 (using citric acid to adjust the pH) and containing high fructose corn syrup. Control samples were balanced to 0.1% ethanol final.

Table 9 presents the sensory results using sucrose as the sweetener. In samples containing the test compound, the test compound was present at a concentration of 10 ppm or less and the concentration of sucrose was 6%. This table indicates the sucrose-alone concentration having a perceived sweetness intensity equivalent to the sweetness intensity of the combination of test compound and sucrose. An "A" value indicates an equivalent sucrose concentration greater than 6% and less than 10%. A "B" value indicates an equivalent sucrose concentration of 10% or greater.

TABLE 9

| Compound | Equivalent Sucrose Conc. |
|---|---|
| 100 | B |
| 101 | A |
| 201 | A |
| 300 | B |
| 305 | B |
| 306 | B |
| 307 | B |
| 309 | B |
| 310 | B |
| 311 | A |
| 700 | B |

Compounds 306, 307, 310, and 311 were also tested using high-fructose corn syrup (HFCS) as the sweetener. In samples containing the test compound, the test compound was present at a concentration of 10 ppm or less and the concentration of HFCS was 6%. The HFCS-alone concentration having a perceived sweetness intensity equivalent to the sweetness intensity of the combination of test compound and HFCS was greater than 6% for all compounds.

Compounds exhibiting T1R2/T1R3 agonistic activity in the receptor-based assay were also evaluated to determine their inherent sweetness threshold. Compounds 201, 300, 305, 306, 307, 309, 310, 311, and 700 were tested for inherent sweetness. All of these compounds had a sweetness intensity at 10 ppm that was less than the sweetness intensity of a 1.5% sucrose solution.

Although the invention has been described with reference to embodiments and examples, it should be understood that numerous and various modifications can be made without departing from the spirit of the invention. Accordingly, the invention is limited only by the following claims.

What is claimed is:
1. A compound having the structure of formula (I):

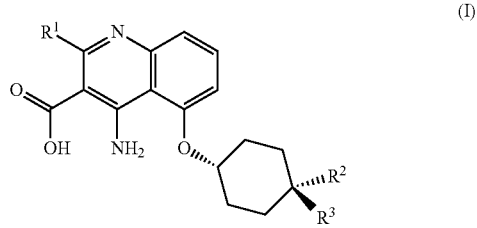

or a physiologically acceptable salt thereof, wherein:
$R^1$ is selected from the group consisting of a hydrogen atom, unsubstituted $C_{1-6}$ alkyl, and $C_{1-6}$ alkyl substituted with $C_{1-6}$ alkoxy or —OH;
$R^2$ is selected from the group consisting of a hydrogen atom, —OH, $C_{1-6}$ alkoxy, unsubstituted $C_{1-6}$ alkyl, and $C_{1-6}$ alkyl substituted with $C_{1-6}$ alkoxy;
$R^3$ is selected from the group consisting of $(CH_2)_n NHC(=O)R^4$, $-(CH_2)_n NR^5 R^6$, and $-(CH_2)_n C(=O)NR^5 R^6$;
n is 0, 1, 2 or 3;
$R^4$ is methyl substituted with one or two $R^{4A}$;
each $R^{4A}$ is independently selected from the group consisting of —$NR^7R^8$; —$SR^9$; and —$OR^9$;
$R^5$ is a hydrogen atom;
$R^6$ is selected from the group consisting of unsubstituted 5-10 membered heteroaryl; and 5-10 membered heteroaryl substituted with one or two groups selected from the group consisting of a halogen atom, $C_1$-$C_6$ alkyl, $C_1$-$C_6$ alkoxy, and amino;
$R^7$ is selected from the group consisting of a hydrogen atom, —C(=O)$OR^{10}$, $C_{1-6}$ alkyl, $C_{3-7}$ carbocyclyl, aryl, 5-10 membered heteroaryl, and 3-10 membered heterocyclyl;
$R^8$ is selected from the group consisting of a hydrogen atom, $C_{1-6}$ alkyl, $C_{3-7}$ carbocyclyl, aryl, 5-10 membered heteroaryl, and 3-10 membered heterocyclyl;
$R^9$ is selected from the group consisting of a hydrogen atom; $C_{1-6}$ alkyl; $C_{3-7}$ carbocyclyl; $C_{3-7}$ carbocyclyl substituted with $C_1$-$C_6$ alkyl; aryl; 5-10 membered heterocyclyl; 3-10 membered heterocyclyl; $C_3$-$C_7$-carbocyclyl($C_1$-$C_6$)alkyl; 3-10 membered heterocyclyl ($C_1$-$C_6$)alkyl; aryl($C_1$-$C_6$)alkyl; and 5-10 membered heteroaryl($C_1$-$C_6$)alkyl;
$R^{10}$ is selected from the group consisting of $C_{1-6}$ alkyl, $C_{3-7}$ carbocyclyl, aryl, 5-10 membered heteroaryl, and 3-10 membered heterocyclyl; and
wherein the physiologically acceptable salt is: hydrochloric acid salt, hydrobromic acid salt, sulfuric acid salt, nitric acid salt, phosphoric acid salt, acetic acid salt, propionic acid salt, glycolic acid salt, pyruvic acid salt, oxalic acid salt, maleic acid salt, malonic acid salt, succinic acid salt, fumaric acid salt, tartaric acid salt, citric acid salt, benzoic acid salt, cinnamic acid salt, mandelic acid salt, methanesulfonic acid salt, ethanesulfonic acid salt, p-toluenesulfonic acid salt, salicylic acid salt, sodium salt, potassium salt, lithium salt, ammonium salt, calcium salt, magnesium salt, iron salt, zinc salt, copper salt, manganese salt, aluminum salt, isopropylamine salt, trimethylamine salt, diethylamine salt, triethylamine salt, tripropylamine salt, or ethanolamine salt.

2. The compound of claim 1 having the structure of formula (Ia):

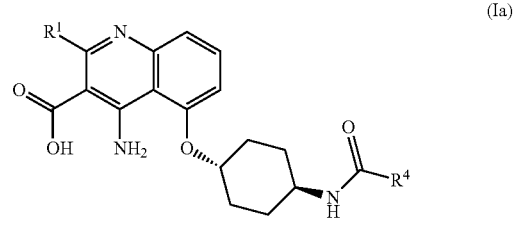

or a physiologically acceptable salt thereof, wherein $R^1$ is selected from the group consisting of a hydrogen atom, unsubstituted C1-6 alkyl, and C1-6 alkyl substituted with C1-6 alkoxy.

3. The compound of claim 2, wherein
$R^4$ is methyl substituted with one or two —$OR^9$; and
$R^9$ is $C_{1-6}$ alkyl.

4. The compound of claim 1, wherein:
$R^4$ is methyl substituted with —$NR^7R^8$;
$R^7$ is a hydrogen atom or —C(=O)$OR^{10}$; and
$R^8$ is selected from the group consisting of a hydrogen atom and $C_{1-3}$ alkyl.

5. The compound of claim 4, wherein:
$R^4$ is methyl substituted with —$NR^7R^8$; and $R^7$ is —C(=O)$OR^{10}$.

6. The compound of claim 1, wherein:
$R^4$ is methyl substituted with —OH or —$NR^7R^8$;
$R^7$ is a hydrogen atom; and
$R^8$ is selected from the group consisting of a hydrogen atom and $C_{1-3}$ alkyl.

7. The compound of claim 1, wherein:
$R^4$ is methyl substituted with —$OR^9$; and $R^9$ is selected from the group consisting of a hydrogen atom, $C_{1-6}$ alkyl, $C_{3-7}$ carbocyclyl, 3-10 membered heterocyclyl, and $C_3$-$C_6$-carbocyclyl-$C_1$-$C_3$-alkyl.

8. The compound of claim 1 having the structure of formula (Iaa):

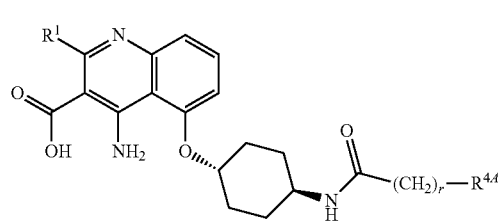

(Iaa)

or a physiologically acceptable salt thereof, wherein:
r is 1;
$R^{4A}$ is selected from the group consisting of —$NR^7R^8$, —$SR^9$, and —$OR^9$;
$R^7$ is selected from the group consisting of a hydrogen atom, —C(=O)$OR^{10}$ and $C_{1-6}$ alkyl;
$R^8$ is selected from the group consisting of a hydrogen atom, $C_{1-6}$ alkyl and $C_{3-7}$ carbocyclyl;
$R^9$ is selected from the group consisting of a hydrogen atom, $C_{1-6}$ alkyl, $C_{3-7}$ carbocyclyl, 3-10 membered heterocyclyl, $C_3$-$C_7$-carbocyclyl($C_1$-$C_6$)alkyl, 3-10 membered heterocyclyl($C_1$-$C_6$)alkyl, and 5-10 membered heteroaryl($C_1$-$C_6$)alkyl; and
$R^{10}$ is selected from the group consisting of $C_{1-6}$ alkyl and $C_{3-7}$ carbocyclyl.

9. The compound of claim 8, wherein:
$R^{4A}$ is —$NR^7R^8$;
$R^7$ is —C(=O)$OR^{10}$;
$R^8$ is selected from the group consisting of a hydrogen atom and $C_{1-3}$ alkyl; and
$R^{10}$ is selected from the group consisting of $C_{1-4}$ alkyl and $C_{3-4}$ carbocyclyl.

10. The compound of claim 8, wherein:
$R^{4A}$ is —$SR^9$ or —$OR^9$; and
$R^9$ is selected from the group consisting of a hydrogen atom, $C_{1-4}$ alkyl, $C_{3-6}$ carbocyclyl, 3-6 membered heterocyclyl, and $C_3$-$C_6$-carbocyclyl($C_1$-$C_3$)alkyl.

11. The compound of claim 10, wherein $R^{4A}$ is —$SR^9$; and $R^9$ is $C_{1-4}$ alkyl.

12. The compound of claim 10, wherein $R^{4A}$ is —$OR^9$; and $R^9$ is selected from the group consisting of a hydrogen atom, $C_{1-4}$ alkyl, $C_{3-6}$ carbocyclyl, 4-6 membered heterocyclyl, and $C_3$-$C_5$-carbocyclyl($C_1$-$C_2$)alkyl.

13. The compound of claim 1 having the structure of formula (Iab):

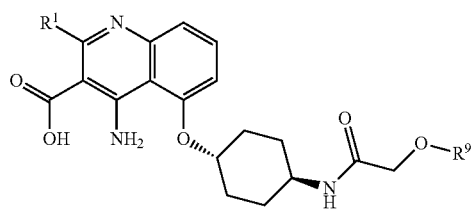

(Iab)

or a physiologically acceptable salt thereof, wherein:
$R^9$ is selected from the group consisting of a hydrogen atom; $C_{1-6}$ alkyl; $C_{3-7}$ carbocyclyl; 3-10 membered heterocyclyl; and $C_3$-$C_7$-carbocyclyl($C_1$-$C_6$)alkyl.

14. The compound of claim 13, wherein $R^9$ is selected from the group consisting of a hydrogen atom, $C_{1-6}$ alkyl, and $C_{3-7}$ carbocyclyl.

15. The compound of claim 1 having the structure of formula (Ib):

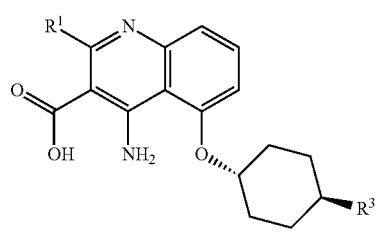

(Ib)

or a physiologically acceptable salt thereof, wherein:
$R^1$ is a hydrogen atom, unsubstituted $C_{1-6}$ alkyl, or $C_{1-6}$ alkyl substituted with $C_{1-6}$ alkoxy;
$R^3$ is —$NHR^6$; and
$R^6$ is a 5-6 membered heteroaryl.

16. The compound of claim 15, wherein $R^6$ is pyridin-2-yl or pyrimidin-2-yl.

17. A compound having the structure of formula (II):

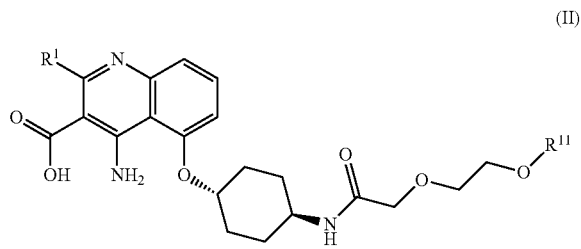

(II)

or a physiologically acceptable salt thereof, wherein:
$R^1$ is selected from the group consisting of a hydrogen atom, unsubstituted $C_{1-6}$ alkyl, and $C_{1-6}$ alkyl substituted with $C_{1-6}$ alkoxy or —OH;
$R^{11}$ is selected from the group consisting of a hydrogen atom, $C_{1-6}$ alkyl, and arylalkyl; wherein the arylalkyl is unsubstituted, or is substituted with one or more substituents selected from the group consisting of a halogen atom, $C_1$-$C_4$ alkyl, $C_1$-$C_4$ alkoxy, $C_1$-$C_4$ haloalkyl, and $C_1$-$C_4$ haloalkoxy; and
wherein the physiologically acceptable salt is: hydrochloric acid salt, hydrobromic acid salt, sulfuric acid salt, nitric acid salt, phosphoric acid salt, acetic acid salt, propionic acid salt, glycolic acid salt, pyruvic acid salt, oxalic acid salt, maleic acid salt, malonic acid salt, succinic acid salt, fumaric acid salt, tartaric acid salt, citric acid salt, benzoic acid salt, cinnamic acid salt, mandelic acid salt, methanesulfonic acid salt, ethanesulfonic acid salt, p-toluenesulfonic acid salt, salicylic acid salt, sodium salt, potassium salt, lithium salt, ammonium salt, calcium salt, magnesium salt, iron salt, zinc salt, copper salt, manganese salt, aluminum salt, isopropylamine salt, trimethylamine salt, diethylamine salt, triethylamine salt, tripropylamine salt, or ethanolamine salt.

18. The compound of claim 17, wherein $R^{11}$ is methyl, ethyl, isopropyl, or benzyl.

19. The compound of claim 17, wherein $R^1$ is a hydrogen atom, methyl, ethyl, or —$CH_2OCH_3$.

20. A compound selected from the group consisting of:
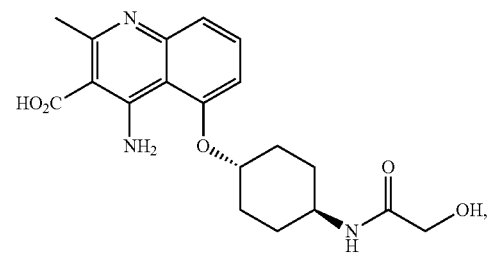
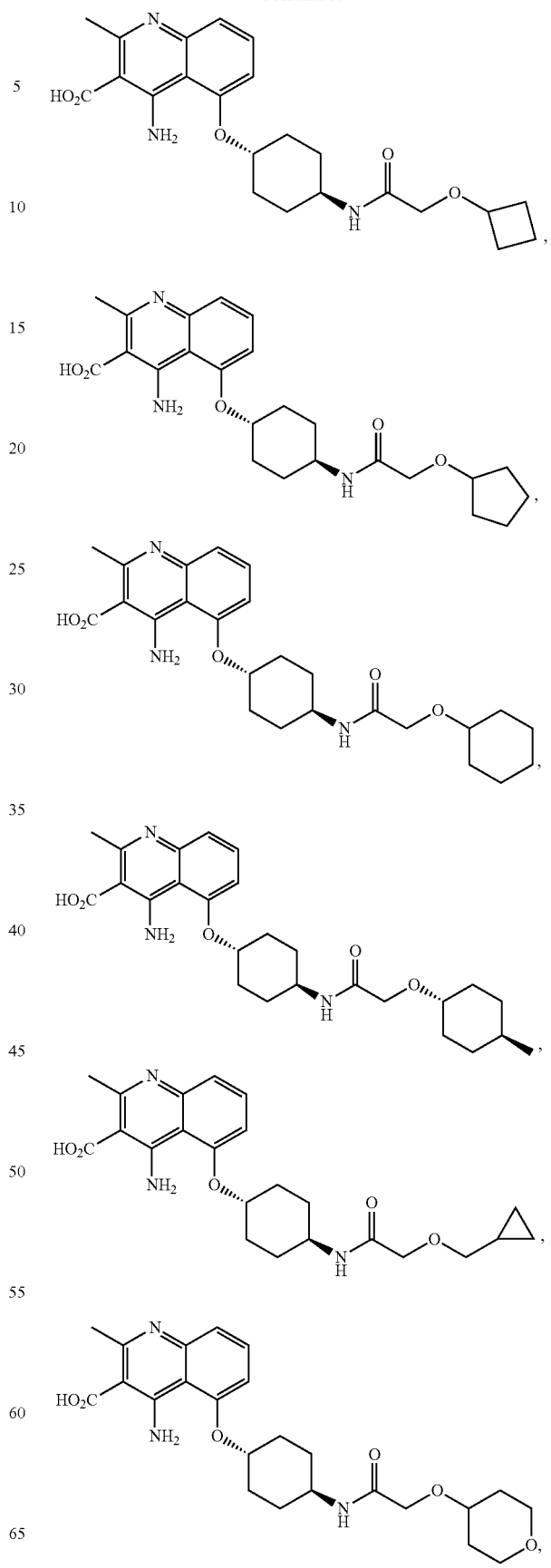

89
-continued
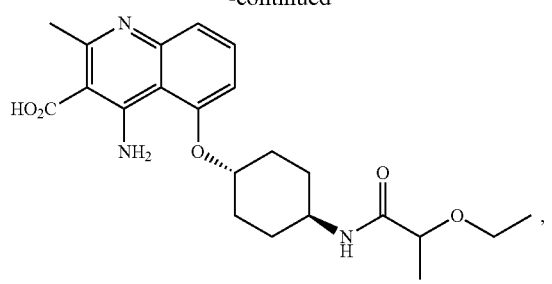
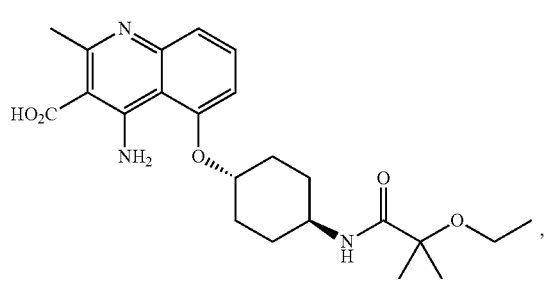
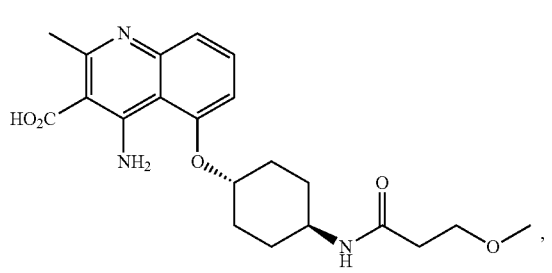
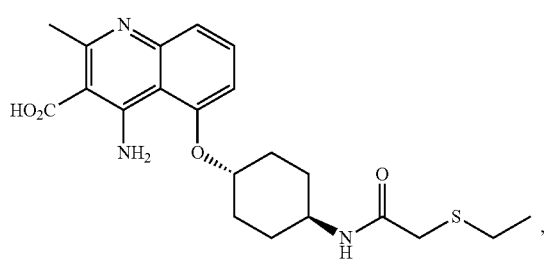
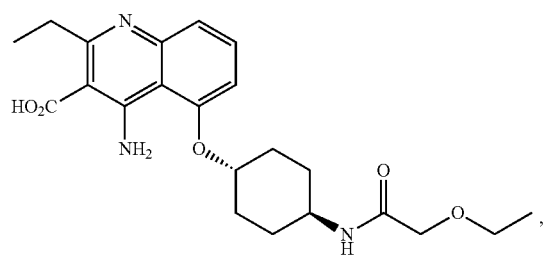
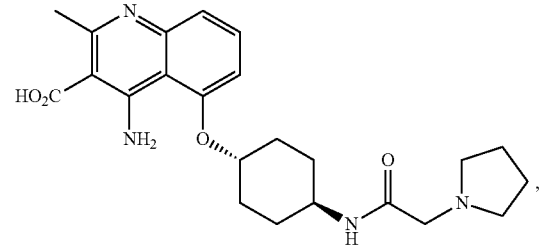
90
-continued
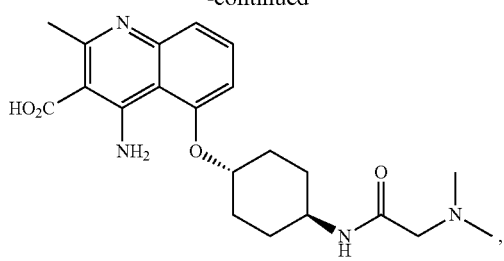
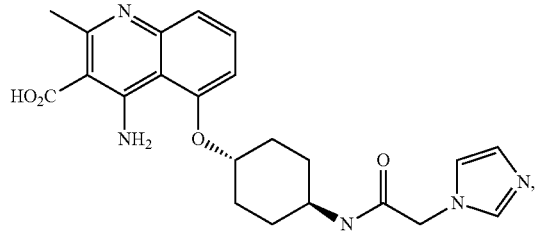
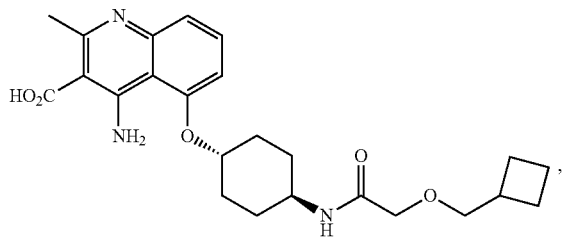
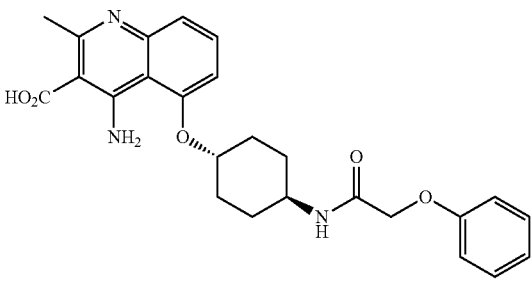
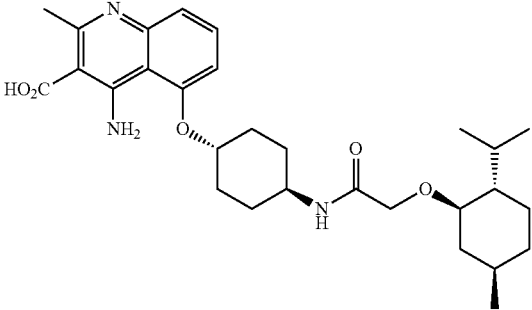
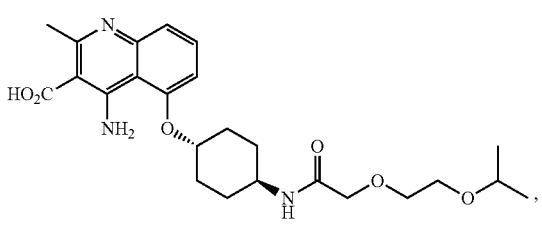

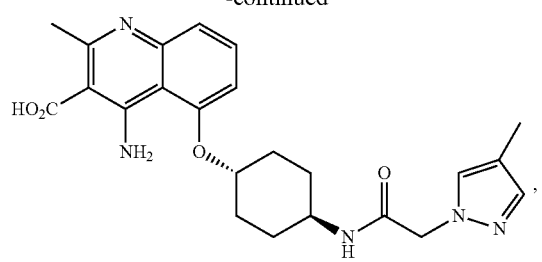
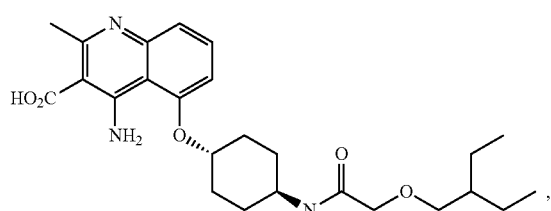
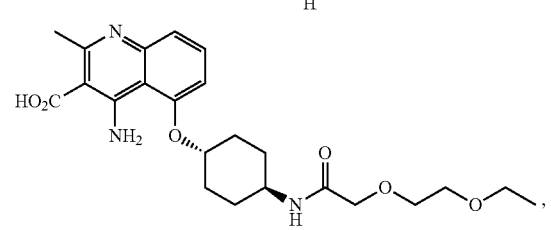
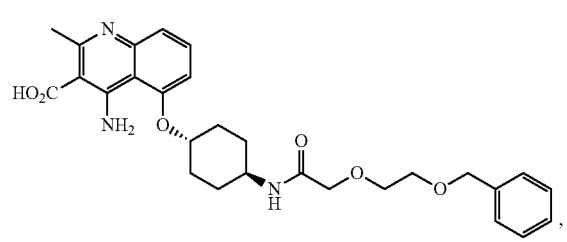
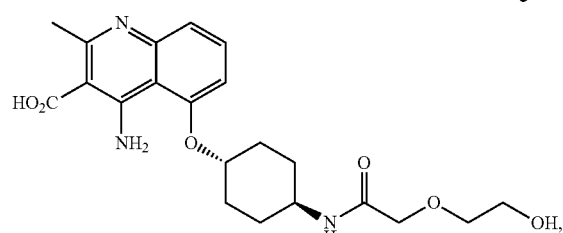
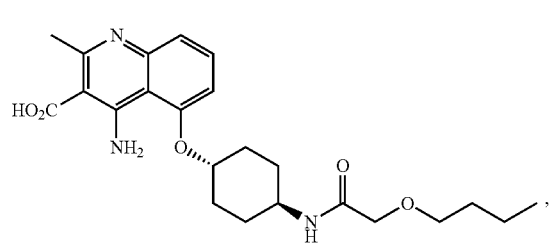
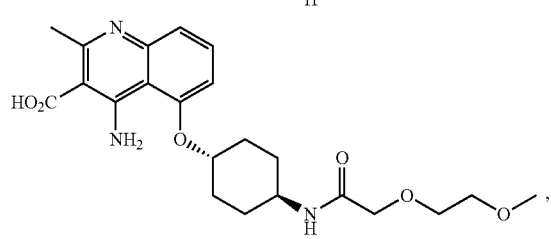
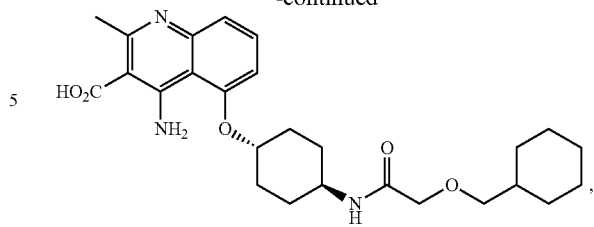
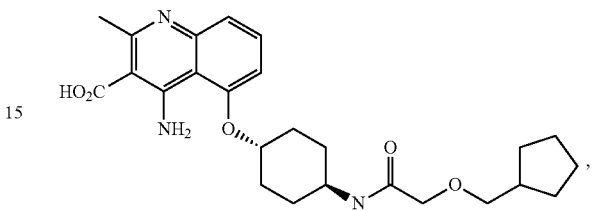
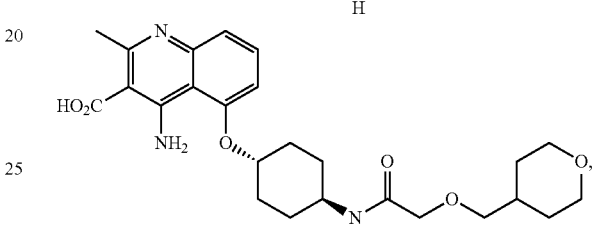
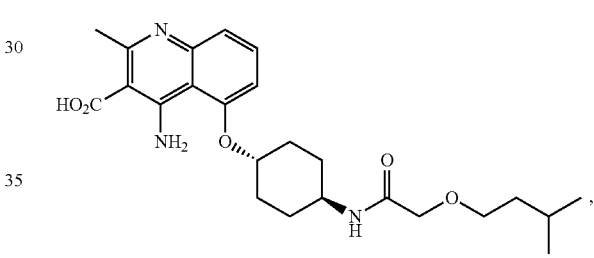
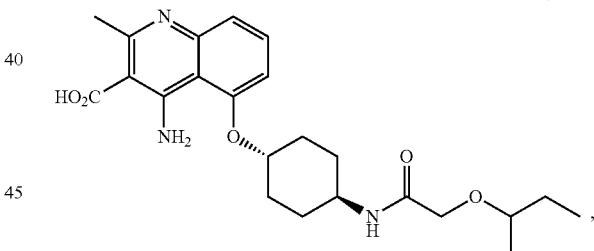
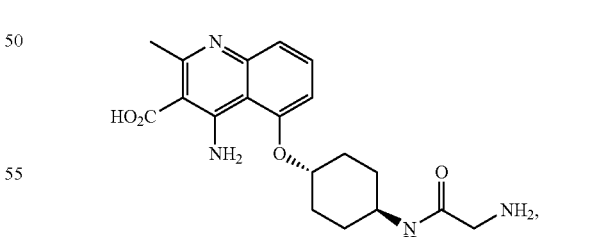
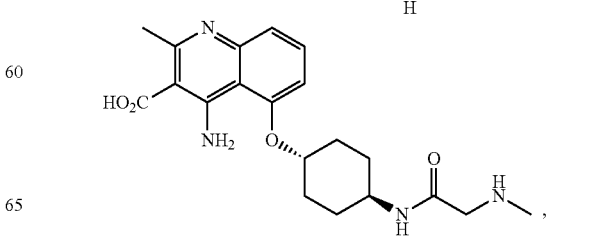

93
-continued
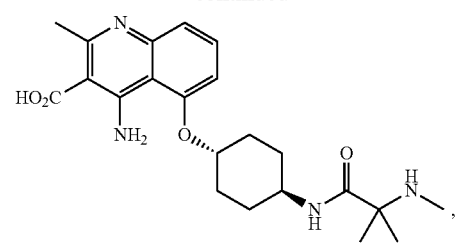
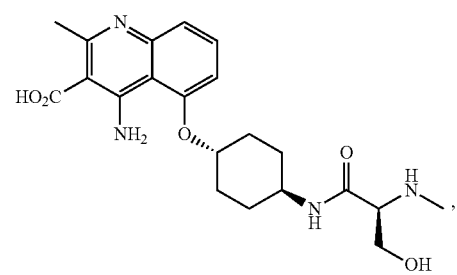
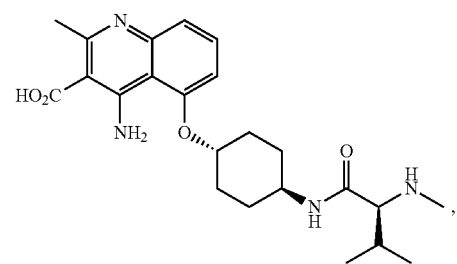
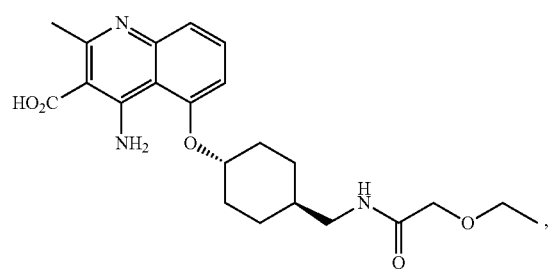
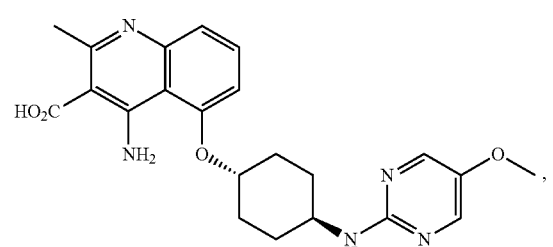
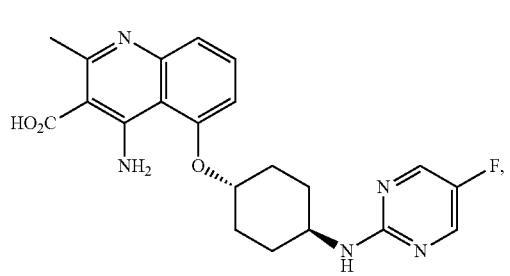
94
-continued
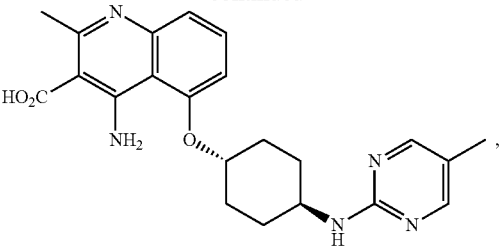
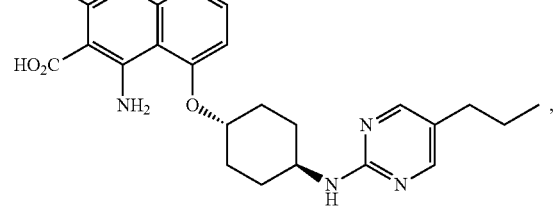
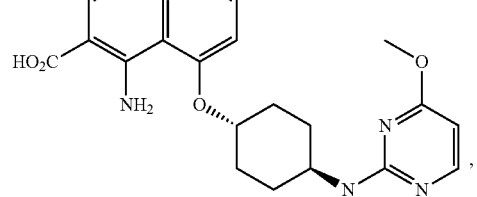
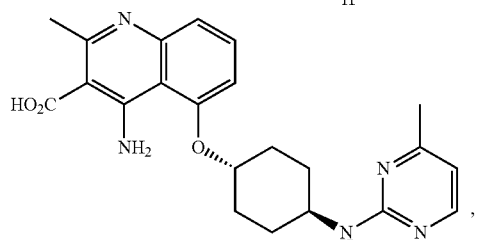
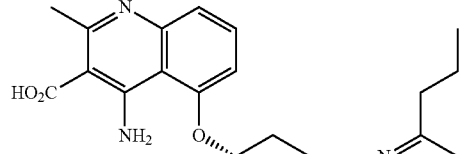
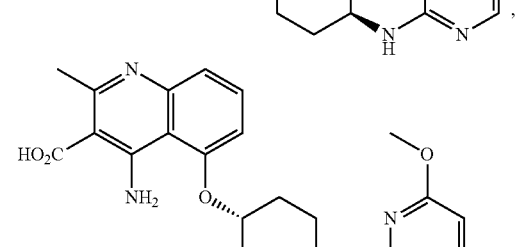
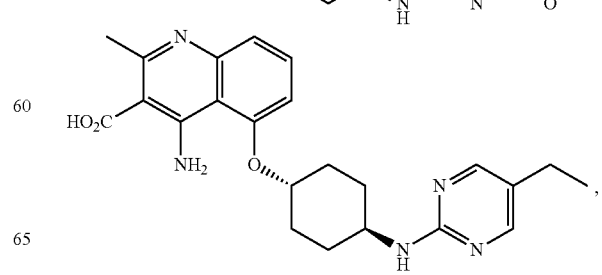

-continued

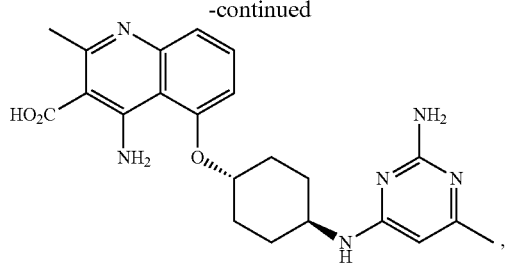

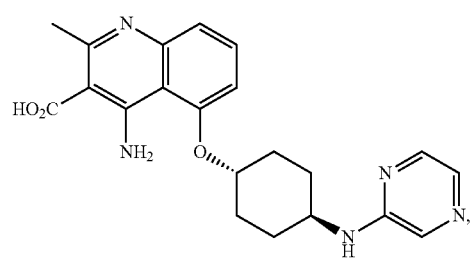

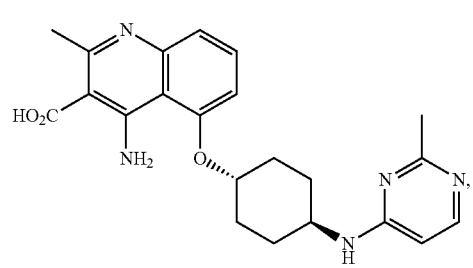

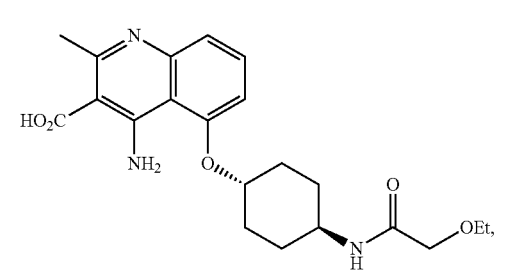

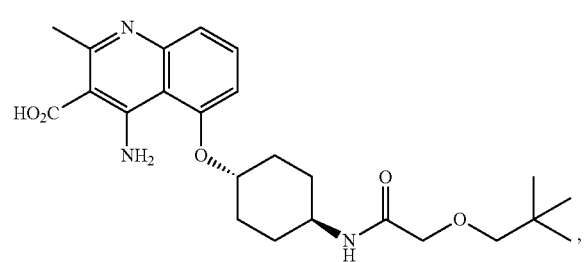

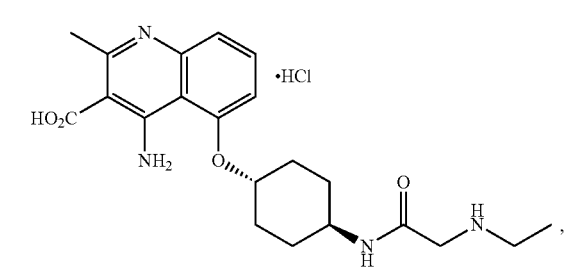

-continued

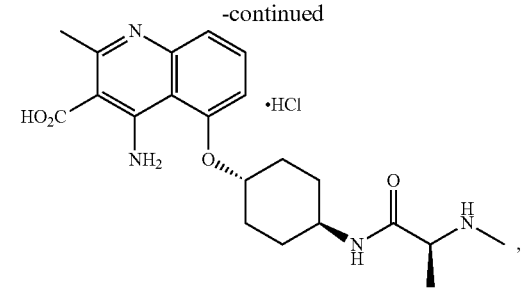

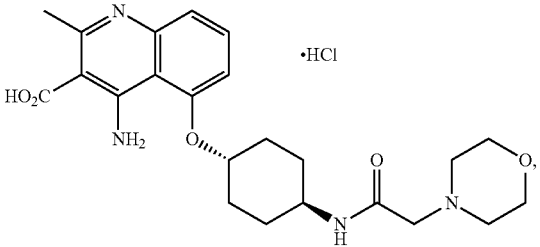

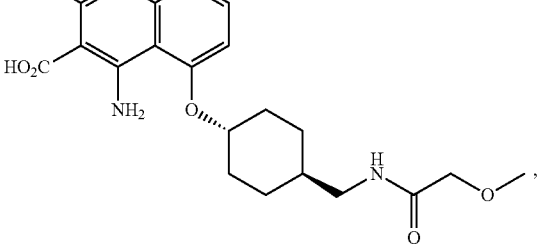

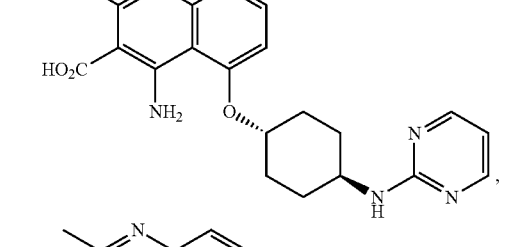

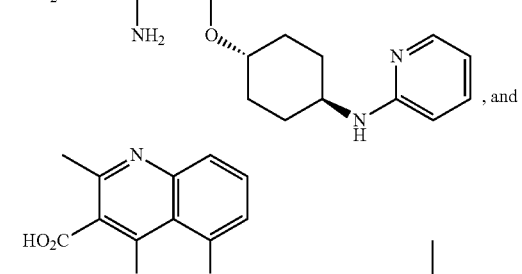

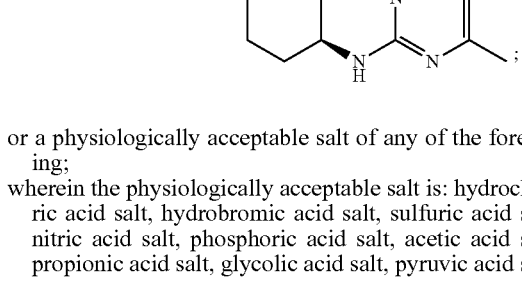

or a physiologically acceptable salt of any of the foregoing;

wherein the physiologically acceptable salt is: hydrochloric acid salt, hydrobromic acid salt, sulfuric acid salt, nitric acid salt, phosphoric acid salt, acetic acid salt, propionic acid salt, glycolic acid salt, pyruvic acid salt, oxalic acid salt, maleic acid salt, malonic acid salt, succinic acid salt, fumaric acid salt, tartaric acid salt, citric acid salt, benzoic acid salt, cinnamic acid salt, mandelic acid salt, methanesulfonic acid salt, ethanesulfonic acid salt, p-toluenesulfonic acid salt, salicylic acid salt, sodium salt, potassium salt, lithium salt, ammonium salt, calcium salt, magnesium salt, iron salt, zinc salt, copper salt, manganese salt, aluminum salt, isopropylamine salt, trimethylamine salt, diethylamine salt, triethylamine salt, tripropylamine salt, or ethanolamine salt.

21. An ingestible composition, comprising the compound of claim 1 and a sweetener.

22. The composition of claim 21, further comprising a vehicle.

23. The composition of claim 22, wherein the vehicle is water.

24. The composition claim 21, wherein the compound is present at a concentration at or below its sweetness recognition threshold.

25. The composition of claim 21, wherein the sweetener is present in an amount from about 0.1% to about 12% by weight.

26. The composition of claim 21, wherein the sweetener is present in an amount from about 2% to about 8% by weight.

27. The composition of claim 21, wherein the sweetener is a sugar.

28. The composition of claim 27, wherein the sweetener is sucrose.

29. The composition of claim 27, wherein the sweetener comprises a combination of fructose and glucose.

30. The composition of claim 21, wherein the sweetener is sucralose.

31. The composition of claim 21, wherein the composition is a beverage.

32. The composition of claim 31, wherein the beverage is selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies.

33. The composition of claim 31, wherein the beverage is a soft drink.

34. A method of enhancing sweetness of a sweetener, comprising combining the compound of claim 1 with the sweetener.

35. The method of claim 34, wherein the sweetener is a sugar.

36. The method of claim 35, wherein the sweetener is sucrose.

37. The method of claim 35, wherein the sweetener comprises a combination of fructose and glucose.

38. The method of claim 34, wherein the sweetener is sucralose.

* * * * *

UNITED STATES PATENT AND TRADEMARK OFFICE
CERTIFICATE OF CORRECTION

| | |
|---|---|
| PATENT NO. | : 11,339,128 B2 |
| APPLICATION NO. | : 14/925793 |
| DATED | : May 24, 2022 |
| INVENTOR(S) | : Petrovic et al. |

It is certified that error appears in the above-identified patent and that said Letters Patent is hereby corrected as shown below:

In the Claims

In Column 84, Claim 1, Lines 1-2, "heterocyclyl ($C_1$-$C_6$)" and insert --heterocyclyl($C_1$-$C_6$)--.

In Column 84, Claim 2, Line 39, delete "C1-6" and insert --$C_{1-6}$--.

In Column 84, Claim 2, Line 39, delete "C1-6" and insert --$C_{1-6}$--.

In Column 84, Claim 2, Line 40, delete "C1-6" and insert --$C_{1-6}$--.

In Column 97, Claim 24, Line 17, after "composition" insert --of--.

Signed and Sealed this
Eleventh Day of October, 2022

Katherine Kelly Vidal
*Director of the United States Patent and Trademark Office*